(12) United States Patent
Hareland

(10) Patent No.: US 11,559,689 B2
(45) Date of Patent: Jan. 24, 2023

(54) NOISE DETECTION AND MODULATION OF CLOSED-LOOP THERAPY ACTION

(71) Applicant: Medtronic, Inc., Minneapolis, MN (US)

(72) Inventor: Scott A. Hareland, Lino Lakes, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 66 days.

(21) Appl. No.: 17/039,040

(22) Filed: Sep. 30, 2020

(65) Prior Publication Data

US 2022/0096839 A1 Mar. 31, 2022

(51) Int. Cl.
*A61N 1/36* (2006.01)
*A61N 1/372* (2006.01)
*A61N 1/02* (2006.01)

(52) U.S. Cl.
CPC ......... *A61N 1/36135* (2013.01); *A61N 1/025* (2013.01); *A61N 1/36062* (2017.08); *A61N 1/36125* (2013.01); *A61N 1/36132* (2013.01); *A61N 1/36139* (2013.01); *A61N 1/37235* (2013.01)

(58) Field of Classification Search
None
See application file for complete search history.

(56) References Cited

U.S. PATENT DOCUMENTS

| | | |
|---|---|---|
| 7,574,259 B1 | 8/2009 | Pei et al. |
| 8,217,523 B2 | 7/2012 | Brown et al. |
| 9,026,212 B2 | 5/2015 | Imran |
| 9,847,739 B2 | 12/2017 | Deterre et al. |
| 9,872,757 B2 | 1/2018 | Kelly et al. |
| 9,884,180 B1 | 2/2018 | Ho et al. |

(Continued)

FOREIGN PATENT DOCUMENTS

| | | |
|---|---|---|
| CN | 108310649 A | 7/2018 |
| WO | 2018080754 A1 | 5/2018 |

(Continued)

OTHER PUBLICATIONS

U.S. Appl. No. 17/038,989, filed Sep. 30, 2020, naming inventors Hareland et al.
Baranth, H., "New Pacemaker Harvests Energy from the Heart," Scientific American, May 2019, 4 pp.
Cadei et al., "Kinetic and Thermal Energy Harvesters for Implantable Medical Devices and Biomedical Autonomous Sensors," Measurement Science and Technology, vol. 25, Nov. 2013, 14 pp.

(Continued)

*Primary Examiner* — Paula J Stice
(74) *Attorney, Agent, or Firm* — Shumaker & Sieffert, P.A.

(57) ABSTRACT

A medical device with closed-loop responsive stimulation may include techniques to mitigate the impact on the therapy output of noise coupled into the medical device. A medical device according to this disclosure may determine the presence of noise and alter the closed loop policy to provide the necessary therapy to the patient and avoid prolonged under stimulation caused by the noise. The medical device may continue therapy while testing for noise. When the device determines the noise level no longer affects the output therapy, the device may return the closed loop policy to a no-noise mode of operation. The medical device may also include techniques to mitigate the impact of manual adjustment while the medical device is subject to noise or is responding to changes in the patient's physiological signals.

25 Claims, 16 Drawing Sheets

(56) References Cited

U.S. PATENT DOCUMENTS

| | | |
|---|---|---|
| 10,044,218 B2 | 8/2018 | Tiefnig |
| 10,581,344 B2 | 3/2020 | Cottone et al. |
| 2006/0093785 A1 | 5/2006 | Hickle |
| 2008/0114219 A1 | 5/2008 | Zhang et al. |
| 2009/0299421 A1 | 12/2009 | Sawchuk |
| 2010/0049270 A1 | 2/2010 | Pastore et al. |
| 2010/0114221 A1 | 5/2010 | Krause et al. |
| 2011/0304240 A1 | 12/2011 | Meitav et al. |
| 2011/0307032 A1 | 12/2011 | Goetz et al. |
| 2013/0103106 A1 | 4/2013 | Schotzko et al. |
| 2015/0012068 A1 | 1/2015 | Bradley et al. |
| 2015/0112408 A1 | 4/2015 | Kals |
| 2015/0151132 A1 | 6/2015 | Pei et al. |
| 2016/0030749 A1 | 2/2016 | Carcieri et al. |
| 2016/0361551 A1 | 12/2016 | Kaula et al. |
| 2017/0069823 A1 | 3/2017 | Karpelson |
| 2018/0126169 A1 | 5/2018 | Hou et al. |
| 2019/0000332 A1 | 1/2019 | Li et al. |
| 2019/0038902 A1 | 2/2019 | Kaemmerer et al. |
| 2019/0091479 A1 | 3/2019 | Bonnet |
| 2019/0099601 A1 | 4/2019 | Torgerson |
| 2019/0151666 A1 | 5/2019 | Bonnet |
| 2019/0350169 A1 | 11/2019 | Weinrauch et al. |
| 2019/0381325 A1 | 12/2019 | Regnier et al. |
| 2019/0388692 A1 | 12/2019 | Dinsmoor et al. |
| 2019/0393406 A1 | 12/2019 | Chen et al. |
| 2020/1079688 | 6/2020 | Su |
| 2020/0406041 A1 | 12/2020 | Cao et al. |
| 2021/0268296 A1 | 9/2021 | Flakne et al. |
| 2021/0379383 A1* | 12/2021 | Single ............... A61N 1/36139 |

FOREIGN PATENT DOCUMENTS

| | | |
|---|---|---|
| WO | 2019246579 A1 | 12/2019 |
| WO | 2019246582 A1 | 12/2019 |

OTHER PUBLICATIONS

Hannan et al., "Energy Harvesting for the Implantable Biomedical Devices: Issues and Challenges," BioMedical Engineering Online, vol. 13, No. 79, Jun. 2014, 23 pp.

Miadhusoodanan, J., "Inner Workings: Self-Powered Biomedical Devices Tap into the Body's Movements," PNAS, vol. 116, No. 36, Sep. 2019, 3 pp.

Niu et al., "A Universal Self-Charging System Driven by Random Biomechanical Energy for Sustainable Operation of Mobile Electronics," Nature Communications, vol. 6, Article No. 8975, Dec. 2015, 8 pp.

Ouyang et al., "Symbiotic Cardiac Pacemaker," Nature Communications, No. 10, vol. 1, Apr. 2019, 11 pp.

"Energy Harvesting from Moving Organs to Power Medical Implants (Video)," retrieved from https://www.medgadget.com/2014/01/energy-harvesting-from-moving-organs.html, on Mar. 30, 2020, 3 pp.

IEEE 802.11ad, "IEEE Standard for Information Technology—Telecommunications and Information Exchange Between Systems—Local and Metropolitan Area Networks—Specific Requirements—Part 11: Wireless LAN Medium Access Control (MAC) and Physical Layer (PHY) Specifications—Amendment 3: Enhancements for Very High Throughput in the 60 GHz Band", IEEE Computer Society, Dec. 28, 2012, 628 pp.

U.S. Appl. No. 17/039,040, filed Sep. 30, 2020, naming inventors Hareland et al.

U.S. Appl. No. 16/948,748, filed Sep. 30, 2020, naming inventors Li et al.

U.S. Appl. No. 17/100,455, filed Nov. 20, 2020, naming inventors Pulliam et al.

U.S. Appl. No. 62/986,458, filed Mar. 6, 2020, naming inventor Li.

International Search Report and Written Opinion of International Application No. PCT/US2021/052160, dated Feb. 22, 2022, 11 pp.

* cited by examiner

NOISE DETECTION AND MODULATION OF CLOSED-LOOP THERAPY ACTION

TECHNICAL FIELD

This disclosure generally relates to electrical stimulation therapy, and more specifically, control of electrical stimulation therapy.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

SUMMARY

In general, the disclosure describes techniques for implementing closed-loop responsive stimulation in which a medical device may adjust therapy output based on sensed signals. A medical device according to this disclosure may implement techniques to mitigate the impact on the therapy output of noise coupled into the medical device. A medical device according to this disclosure also may implement techniques to mitigate the impact of manual adjustment while the medical device is subject to noise or is responding to changes in the patient's physiological signals.

In one example, this disclosure describes a method includes receiving information indicative of a sensed evoked compound action potential (ECAP) signal; determining a value of a characteristic of the ECAP signal based on the information, wherein the ECAP signal is elicited by a respective stimulation pulse of a plurality of stimulation pulses; executing a closed loop policy that adjusts, based on the value of the characteristic of the ECAP signal, a value of a parameter that at least partially defines stimulation therapy; determining that the value of the characteristic of the ECAP signal is outside of an expected range; and responsive to determining that the value of the characteristic of the ECAP signal is outside of the expected range, disabling the closed loop policy.

In another example, this disclosure describes a medical device comprising processing circuitry configured to: receive information indicative of a sensed evoked compound action potential (ECAP) signal determine a value of a characteristic of the ECAP signal based on the information, wherein the ECAP signal is elicited by respective stimulation pulses of a plurality of pulses; determine whether a value of a characteristic of the ECAP signal is outside of an expected range; execute a closed loop policy, wherein the closed loop policy adjusts a value of a parameter that at least partially defines stimulation therapy, based on the value of the characteristic of the ECAP signal; and responsive to determining that the value of the characteristic of the ECAP signal is outside of the expected range, disable the closed-loop policy.

In another example, this disclosure describes a computer-readable medium comprising instructions for causing programmable processor processing circuitry to: receive information indicative of a sensed evoked compound action potential (ECAP) signal determine a value of a characteristic of the ECAP signal based on the information, wherein the ECAP signal is elicited by respective stimulation pulses of a plurality of pulses; determine whether a value of a characteristic of the ECAP signal is outside of an expected range; execute a closed loop policy, wherein the closed loop policy adjusts a value of a parameter that at least partially defines stimulation therapy, based on the value of the characteristic of the ECAP signal; and responsive to determining that the value of the characteristic of the ECAP signal is outside of the expected range, disable the closed-loop policy.

In one example, this disclosure describes a method includes delivering, by stimulation generation circuitry of a medical device, electrical stimulation therapy to a patient, the electrical stimulation therapy comprising a plurality of pulses defined by a set of parameters; receiving, by processing circuitry of the medical device, a command from an external programmer to change a value of a parameter defining the plurality of pulses, wherein the external programmer is external to the medical device; determining, by the processing circuitry, that the requested change to the parameter is a request to increase the value of the parameter defining the plurality of pulses; determining, by the processing circuitry, that a control policy executed by the processing circuitry is determining values of the parameter that defines the electrical stimulation therapy; responsive to determining that the control policy is determining values of at the parameter that defines the electrical stimulation therapy, rejecting, by the processing circuitry, the request to change the value of the parameter.

In another example, this disclosure describes a medical device includes stimulation generation circuitry configured to deliver electrical stimulation therapy to a patient, the electrical stimulation therapy comprising a plurality of pulses defined by a set of parameters; and processing circuitry configured to: receive a command from an external programmer (1602) to change a value of a parameter defining the plurality of pulses, wherein the external programmer is external to the medical device; determine that the requested change to the parameter is a request to increase the value of the parameter defining the plurality of pulses; determining that a control policy executed by the processing circuitry is determining values of the parameter that defines the electrical stimulation therapy responsive to determining that the control policy is determining values of at the parameter that defines the electrical stimulation therapy, reject the request to change the value of the parameter.

In another example, this disclosure describes a computer-readable medium comprising instructions for causing a programmable processor of a medical device to: cause stimulation generation circuitry of the medical device to deliver electrical stimulation therapy to a patient, the electrical stimulation therapy comprising a plurality of pulses defined by a set of parameters; receive of the medical device, a command from an external programmer to change a value of a parameter defining the plurality of pulses, wherein the external programmer is external to the medical device; determine that the requested change to the parameter is a request to increase the value of the parameter defining the plurality of pulses; determine that a control policy executed by the processing circuitry is determining values of the parameter that defines the electrical stimulation therapy; responsive to determining that the control policy is determining values of at the parameter that defines the electrical stimulation therapy, reject the request to change the value of the parameter.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
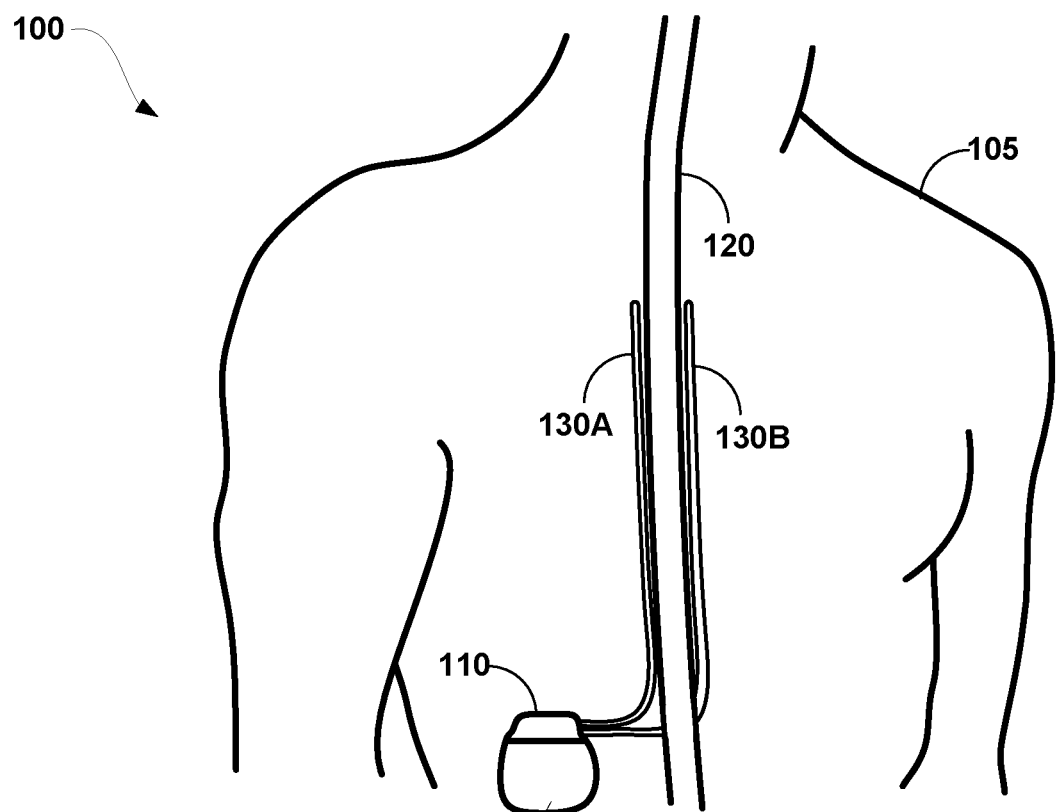
FIG. 1 is a conceptual diagram illustrating an example system that includes an implantable medical device (IMD) configured to deliver spinal cord stimulation (SCS) therapy and an external programmer, in accordance with one or more techniques of this disclosure.

The disclosure describes techniques for implementing closed-loop responsive stimulation in which a medical device may adjust therapy output based on sensed signals. A medical device according to this disclosure may include techniques to mitigate the impact on the therapy output of noise coupled into the medical device.

In some examples, a closed-loop responsive medical device may control electrical stimulation therapy by sensing an evoked compound action potential (ECAP). An ECAPS Responsive Stimulation (ERS) therapy based medical device may be configured to modulate therapy output (e.g., control and adjust one or more parameter values that define therapy) in response to measured ECAPS. Therapy output may be in the form of an electrical stimulation pulse, such as a voltage pulse or a current pulse, defined by a set of therapy parameters, e.g. stimulation amplitude, frequency, pulse width, pulse shape and other parameters. For example, in response to determining that a characteristic of the measured ECAP signal (e.g., a voltage amplitude) has deviated from a target ECAP characteristic, the system may change the values of one or more stimulation parameters of the next one or more output pulses delivered to the patient. For example, the system may increase or decrease a current amplitude or a pulse width of the output electrical stimulation pulse.

In some examples, changes in patient physiology, such as changes in hydration level, patient response to a virus, changes in drug therapy, activity level and many other factors may cause a given output pulse to result in a different measured ECAP. Also, changes in patient posture may change a distance between an implanted electrode and a target nerve. For example, as a patient moves between a supine posture state to a standing posture state or when a patient coughs or sneezes may change relative location of one or more electrodes and a target nerve. An ERS therapy based medical device may include a closed-loop algorithm to reduce the device stimulation output when high ECAP signals are measured to prevent over-stimulation and may lead to patient discomfort. When the sensed ECAP signals reduce, the closed-loop ERS algorithm may return the medical device output settings to default values.

However, a closed-loop responsive medical device may be susceptible to noise, such as external noise that may be coupled into the sensing system that the medical device employs for feedback into closed-loop control. The noise may adversely impact the ability of the medical device to appropriately detect the ECAP signal from patient tissues, such as the system sensing the amplitude of the noise when it is greater than the ECAP signals themselves. In response to the detected noise, the system may respond by reducing stimulation to the patient. Reduced stimulation can lead to under stimulation and resulting patient discomfort from untreated symptoms. In some examples, the patient may have an adjustment tool (e.g., an external programmer) configured to communicate with the medical device to increase or decrease therapy intensity based on the patient's perceived response to the therapy provided by the medical device. A patient may manually increase the default stimulation level using the adjustment tool. In examples in which the patient manually adjusts the default stimulation level while the medical device is reducing stimulation intensity because of the presence of noise, or the medical device is adapting to changes in the patient's physiological signals, when the noise is removed, or when the physiological signals change again, the new default stimulation parameter values may cause the system to deliver inappropriate stimulation (over or under stimulation) resulting in patient discomfort. A medical device according to this disclosure may include techniques to mitigate the impact of noise on the therapy output and mitigate the impact of manual adjustment while the medical device is subject to noise or is responding to changes in the patient's physiological signals. Also, a medical device according to this disclosure may determine the presence of noise and alter the closed-loop algorithm to provide the necessary therapy to the patient and avoid prolonged under stimulation caused by the noise.

The term "stimulation signal" may be used herein to describe a signal that the medical device senses that represents a stimulation pulse delivered by the medical device. This stimulation signal may also be referred to as an "artifact" in the sensed signals. One or more sense electrodes of the medical device may detect a stimulation signal due to one or more stimulation electrodes proximate to the sense electrodes delivering a stimulation pulse. In this way, delivering a stimulation pulse may cause the medical device to sense a respective stimulation signal during a window of time substantially overlapping with the delivery of the stimulation pulse. An electrical potential of the stimulation electrodes during the window of time in which the medical device delivers the stimulation pulse may cause the sensing circuitry of the medical device to generate a sense signal which is representative of the stimulation pulse delivered during the window of time. The stimulation signal is thus representative of electrical potential changes in tissue directly caused by the delivered stimulation pulse. Conversely, an ECAP is a signal representative of physiological action (e.g., depolarizing nerve fibers) caused by the stimulation pulse. In this way, stimulation signals may be at least partially distinguished from ECAPs, since ECAPs represent electrical signals sensed by the medical device due to an excitation of target tissue of the patient in response to the delivery of a stimulation pulse. In other words, an ECAP represents a detected physiological response to a stimulation pulse, and a stimulation signal represents the direct detection of the stimulation pulse itself and associated changes in the charge in tissue.

In some examples, the medical device may deliver stimulation pulses in the form of control pulses and informed pulses. More specifically, electrical stimulation pulses are delivered in the form of informed pulses and control pulses that are at least partially interleaved with each other. Control pulses (e.g., stimulation signal test pulses) are those stimulation pulses that are configured to elicit one or both of a stimulation signal and a detectable ECAP signal. In some examples, control pulses may contribute to the therapy for a patient. In other examples, control pulses do not contribute to the therapy for the patient, e.g., non-therapeutic pulses. In this manner, control pulses may or may not be configured to elicit a therapeutic effect for the patient. Informed pulses are those stimulation pulses that are at least partially defined by one or more parameters based on the detectable stimulation signal elicited from one or more control pulses. In some examples, one or more informed pulses are at least partially defined by one or more parameters based on a respective ECAP elicited from one or more control pulses. In this manner, the informed pulses are "informed" by the ECAP signal detected from a control pulse. Informed pulses are also configured to provide a therapy to a patient, such as paresthesia that relieves pain symptoms.

As described herein, a medical device may be configured to deliver a plurality of informed pulses and/or control pulses configured to provide a therapy to the patient based on one or more parameters of ECAP signals elicited by previously delivered control pulses. The medical device, in some cases, may deliver a plurality of informed pulses, which are configured to provide or at least contribute to a therapy to the patient based on one or more parameters of ECAP signals elicited by control pulses. In some examples, the control pulses may be configured to elicit ECAP signals without contributing to the therapy of the patient. However, in other examples, the control pulses may provide therapy to the patient either alone or in combination with the informed pulses. The control pulses may be interleaved with the delivery of the informed pulses. For example, the medical device may alternate the delivery of informed pulses with control pulses such that a control pulse is delivered, and an ECAP signal is sensed from the control pulses, between consecutive informed pulses. In some examples, multiple control pulses are delivered, and respective ECAP signals sensed, between the delivery of consecutive informed pulses.

In some examples, multiple informed pulses will be delivered between consecutive control pulses. In any case, the informed pulses may be delivered according to a predetermined pulse frequency selected so that the informed pulses can produce or contribute to a therapeutic result for the patient. One or more control pulses are then delivered, and the respective ECAP signals sensed, within one or more time windows between consecutive informed pulses delivered according to the predetermined pulse frequency. The predetermined pulse frequency may be a single consistent frequency or a varied frequency that varies over time. The pulse width of the control pulses may be shorter than the pulse width of the informed pulses to enable the medical device to detect the ECAP signals elicited from the control pulses. Put another way, the longer pulse width of the informed pulses may prevent all phases of the resulting stimulation signals and prevent the resulting ECAP signals from being detected due to, for example, overlapping of the informed pulse with the ECAP signal and the stimulation signal. In this manner, a medical device can administer informed pulses from the medical device uninterrupted while one or both of ECAPs and stimulation signals can be sensed from control pulses delivered during times at which the informed pulses are not being delivered.

In some examples, a pulse frequency of stimulation pulses (e.g., control pulses and/or informed pules) delivered by the medical device may be within a range from 50 Hertz (Hz) to 70 Hz, but this is not required. In some examples, a pulse frequency of stimulation pulses (e.g., control pulses and/or informed pules) delivered by the medical device may be within a range from 0.1 Hz to 100 kilohertz (KHz), The pulse frequency of the stimulation pulses may be within a range from 0.5 KHz to 5 KHz (e.g., 1 KHz) and/or within a range from 5 KHz to 15 KHz (e.g., 10 KHz), as examples. In some examples, when a frequency of control pulses and informed pulses increases, a maximum pulse width of control pulses which do not obscure respective control pulses decreases. These ranges are just examples. In some examples, both control and informed pulses can be delivered over a wide range of frequencies and informed pulses may be interspersed between multiple control pulses.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal than may have a sinusoidal waveform or other continuous waveform.

FIG. 1 is a conceptual diagram illustrating an example system that includes an implantable medical device (IMD) configured to deliver spinal cord stimulation (SCS) therapy and an external programmer, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. The disclosure will refer to an implantable SCS system for purposes of illustration, but the techniques described may also apply, without limitation, to other types of medical devices or other therapeutic applications of medical devices.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. This electrical stimulation may be delivered in the form of stimulation pulses. In some examples, IMD 110 may be configured to generate and deliver stimulation pulses to include control pulses configured to elicit ECAP signals. The control pulses may or may not contribute to therapy in some examples. In some examples, IMD 110 may, in addition to control pulses, deliver informed pulses that contribute to the therapy for the patient, but which do not elicit detectable ECAPs. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be, for example, constant current or constant voltage-based pulses may be delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a leads 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, leads 130 may include a lead extension or other segments that may aid in implantation or positioning of leads 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, and voltage or current amplitude, pulse frequency, pulse width, pulse shape of stimulation delivered by the electrodes. These stimulation parameters of stimulation pulses (e.g., control pulses and/or informed pulses) are typically predetermined parameter values determined prior to delivery of the stimulation pulses (e.g., set according to a stimulation program).

However, in some examples, system 100 changes one or more parameter values automatically based on one or more factors or based on user input.

A test stimulation program may define stimulation parameter values that define control pulses delivered by IMD 110 through at least some of the electrodes of leads 130. These stimulation parameter values may include information identifying which electrodes have been selected for delivery of control pulses, the polarities of the selected electrodes, i.e., the electrode combination for the test stimulation program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each test stimulation program are configured to evoke a compound action potential from nerves. In some examples, the test stimulation program defines when the control pulses are to be delivered to the patient based on the frequency and/or pulse width of the informed pulses when informed pulse are also delivered. In some examples, the stimulation defined by each test stimulation program are not intended to provide or contribute to therapy for the patient. In other examples, the stimulation defined by each test stimulation program may contribute to therapy when the control pulses elicit one or both of detectable ECAP signals. In this manner, the test stimulation program may define stimulation parameters the same or similar to the stimulation parameters of therapy stimulation programs.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, leads 130 includes one or more sensors configured to allow IMD 110 to monitor one or more parameters of patient 105, such as patient activity, pressure, temperature, posture, or other characteristics. The one or more sensors may be provided in addition to, or in place of, therapy delivery by leads 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical, or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 110 generates and delivers electrical stimulation therapy to a target stimulation site within patient 105 via the electrodes of leads 130 to patient 105 according to one or more therapy stimulation programs. A therapy stimulation program defines values for one or more parameters that define an aspect of the therapy delivered by IMD 110 according to that program. For example, a therapy stimulation program that controls delivery of stimulation by IMD 110 in the form of pulses may define values for voltage or current pulse amplitude, pulse width, pulse shape, and pulse rate (e.g., pulse frequency) for stimulation pulses delivered by IMD 110 according to that program.

In some examples where relevant phases of stimulation signals cannot be detected from the types of pulses intended to be delivered to provide therapy to the patient, control pulses and informed pulses may be delivered. For example, IMD 110 is configured to deliver control stimulation in the form of control pulses to patient 105 via a combination of electrodes of leads 130, alone or in combination with an electrode carried by or defined by an outer housing of IMD 110. The tissue targeted by the control stimulation may be the same tissue targeted by the electrical stimulation therapy, delivered in the form of informed pulses. But IMD 110 may deliver control stimulation pulses via the same, at least some of the same, or different electrodes. Since control stimulation pulses are delivered in an interleaved manner with informed pulses, a clinician and/or user may select any desired electrode combination for informed pulses. Like the electrical stimulation therapy, the control stimulation may be in the form of electrical stimulation pulses or continuous waveforms.

In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. In other examples, a control stimulation pulse may include a tri-phasic pulse or pulse having more than three phases. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. In some cases, the control pulses may elicit an ECAP signal from the tissue, and IMD 110 may sense the ECAP signal via two or more electrodes on leads 130. In cases where the control stimulation pulses are applied to spinal cord 120, the signal may be sensed by IMD 110 from spinal cord 120.

IMD 110 may deliver control stimulation to a target stimulation site within patient 105 via the electrodes of leads 130 according to one or more test stimulation programs. The one or more test stimulation programs may be stored in a storage device of IMD 110. Each test program of the one or more test stimulation programs includes values for one or more parameters that define an aspect of the control stimulation delivered by IMD 110 according to each respective test program, such as current or voltage amplitude, pulse width, pulse frequency, electrode combination, and, in some examples, timing based on informed pulses to be delivered to patient 105. In some examples, IMD 110 delivers control stimulation to patient 105 according to multiple test stimulation programs.

A user, such as a clinician (not shown in FIG. 1) or patient 105, may interact with a user interface (not shown in FIG. 1) of external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control electrical stimulation therapy (e.g., informed pulses) and control stimulation (e.g., control pulses). For example, external programmer 150 may transmit therapy stimulation programs, test stimulation programs, stimulation parameter adjustments, therapy stimulation program selections, test program selections, user input, or other information to control the operation of IMD 110, e.g., by wireless telemetry or wired connection. As described herein, stimulation delivered to the patient may include control pulses, and, in some examples, stimulation may include control pulses and informed pulses.

In some cases, external programmer 150 may be called a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

Efficacy of electrical stimulation therapy may, in some cases, be indicated by one or more characteristics (e.g. an amplitude of or between one or more peaks or an area under the curve of one or more peaks) of an action potential that is evoked by a stimulation pulse delivered by IMD 110 (i.e., a characteristic of the ECAP signal). In one or more cases where stimulation pulses elicit detectible ECAPs, electrical stimulation therapy delivery by leads 130 of IMD 110 may cause neurons within the target tissue to evoke a compound action potential that travels up and down the target tissue (e.g., nerve fibers), eventually arriving at sensing electrodes of IMD 110. Furthermore, control stimulation may also elicit at least one ECAP, and ECAPs responsive to control stimulation may also be a surrogate for the effectiveness of the therapy. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse over time. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control stimulation pulses.

In the example of FIG. 1, IMD 110 may perform a plurality of processing and computing functions. However, external programmer 150 instead may perform one, several, or all of these functions. In this alternative example, IMD 110 may relay sensed signals to external programmer 150 for analysis, and external programmer 150 may transmit instructions to IMD 110 to adjust the one or more parameters defining the electrical stimulation therapy based on analysis of the sensed signals. For example, IMD 110 may relay the sensed signal indicative of the sensed ECAP signal to external programmer 150.

Figure 2:
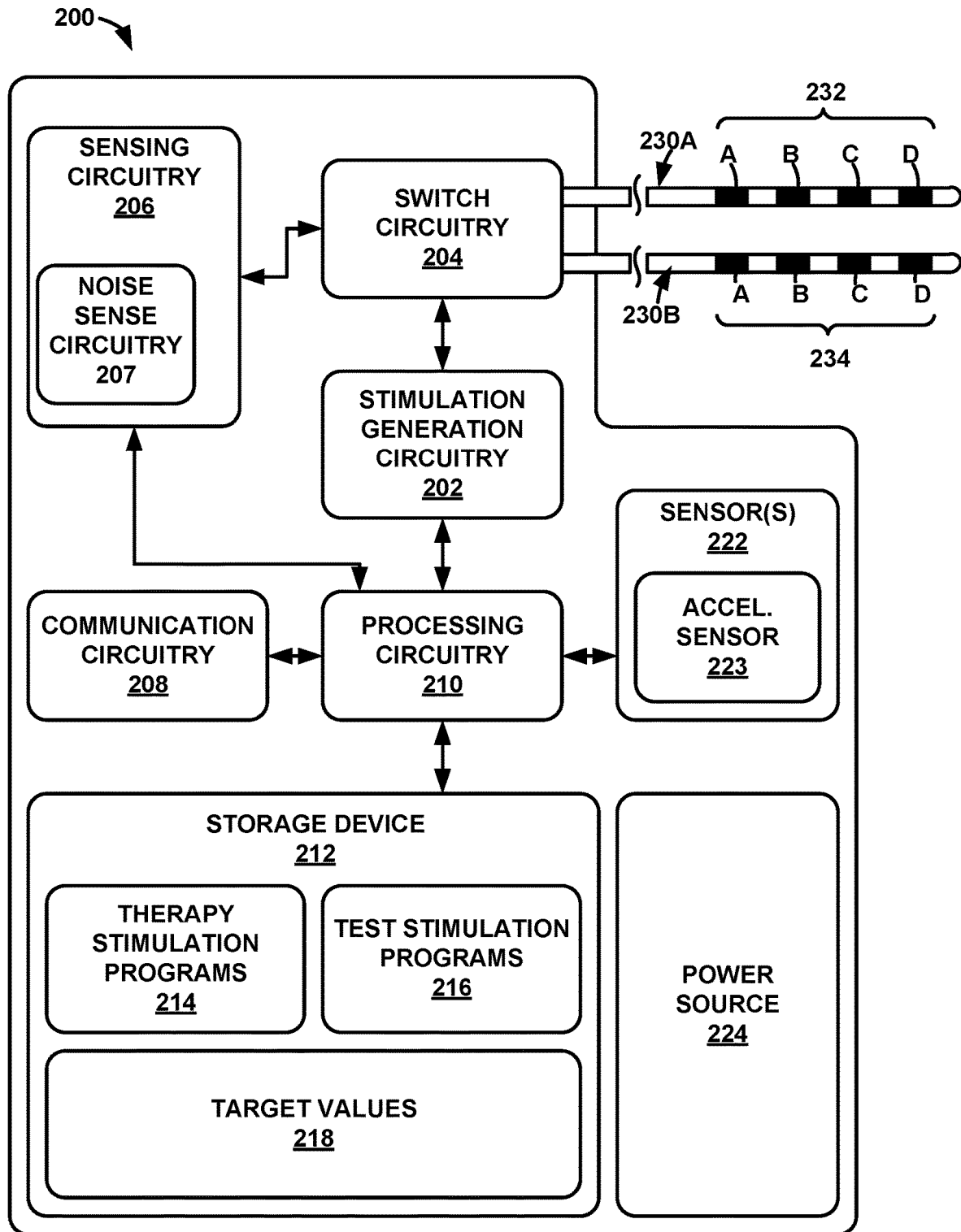
FIG. 2 is a block diagram illustrating an example configuration of components of the IMD of FIG. 1, in accordance with one or more techniques of this disclosure.

FIG. 2 is a block diagram illustrating an example configuration of components of IMD 200, in accordance with one or more techniques of this disclosure. IMD 200 may be an example of IMD 110 of FIG. 1. In the example shown in FIG. 2, IMD 200 includes stimulation generation circuitry 202, switch circuitry 204, sensing circuitry 206, communication circuitry 208, processing circuitry 210, storage device 212, sensor(s) 222, and power source 224. As seen in FIG. 2, sensor(s) 222 include acceleration sensor 223.

In the example shown in FIG. 2, storage device 212 stores therapy stimulation programs 214 and test stimulation programs 216 in separate memories within storage device 212 or separate areas within storage device 212. Each stored therapy stimulation program of therapy stimulation programs 214 defines values for a set of electrical stimulation parameters (e.g., a stimulation parameter set), such as a stimulation electrode combination, electrode polarity, current or voltage amplitude, pulse width, pulse rate, and pulse shape. Each stored test stimulation programs 216 defines values for a set of electrical stimulation parameters (e.g., a control stimulation parameter set), such as a stimulation electrode combination, electrode polarity, current or voltage amplitude, pulse width, pulse rate, and pulse shape. Test stimulation programs 216 may also have additional information such as instructions regarding when to deliver control pulses based on the pulse width and/or frequency of the informed pulses defined in therapy stimulation programs 214. In examples in which control pulses are provided to the patient without the need for informed pulses, a separate test stimulation program may not be needed. Instead, the test stimulation program for therapy that only includes control pulses may define the same control pulses as the corresponding therapy stimulation program for those control pulses.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or directed sensed signals from one or more of electrodes 232, 234 to sensing circuitry 206. In other examples, stimulation generation circuitry 202 and/or sensing circuitry 206 may include sensing circuitry to direct signals to and/or from one or more of electrodes 232, 234, which may or may not also include switch circuitry 204.

Sensing circuitry 206 monitors signals from any combination of electrodes 232, 234. In some examples, sensing circuitry 206 includes one or more amplifiers, filters, and analog-to-digital converters. Sensing circuitry 206 may be used to sense physiological signals, such as ECAPs. Additionally, or alternatively, sensing circuitry 206 may sense one or more stimulation pulses delivered to patient 105 via electrodes 232, 234. In some examples, sensing circuitry 206 detects electrical signals, such as stimulation signals and/or ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Communication circuitry 208, in the example of FIG. 2, supports communication, including wireless communication, between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via communication circuitry 208. Updates to the therapy stimulation programs 214 and test stimulation programs 216 may be stored within storage device 212. Communication circuitry 208 in IMD 200, as well as communication circuits in other devices and systems described herein, such as the external programmer, may accomplish communication by radiofrequency (RF) communication techniques. In addition, communication circuitry 208 may communicate with an external medical device programmer (not shown in FIG. 2) via proximal inductive interaction of IMD 200 with the external programmer. The external programmer may be one example of external programmer 150 of FIG. 1. Accordingly, communication circuitry 208 may send information to the external programmer on a continuous basis, at periodic intervals, or upon request from 1 MB 200 or the external programmer. In some examples, communication circuitry 208 may also support communication between other medical devices, either implanted in, worn by or in proximity to patient 105 depicted in FIG. 1.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to therapy stimulation programs 214 and test stimulation programs 216 stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 210 also controls stimulation generation circuitry 202 to generate and apply the stimulation signals to selected combinations of electrodes 232, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques. Processing circuitry 210 may be configured to receive information indicative of a sensed ECAP signal via sensing circuitry 206. In some examples, processing circuitry may receive an analog signal from sensing circuitry 206. In other examples, processing circuitry 210 may receive a digital signal.

In some examples, sensing circuitry 206 may include specific noise sensing circuitry 207. Noise sensing circuitry 207 may include one or more bandpass filters, band stop filters, amplifiers, analog and digital analysis circuitry, and related circuitry configured to detect noise that could couple onto leads 230 and be received by sensing circuitry 206. In some examples, noise sensing circuitry 207 may be configured to detect specific noise signals, such as 60 Hz signals, 50 Hz signals, or other expected noise signals. Noise sensing circuitry 207 may provide an indication to processing circuitry 210 that noise is present and that the ECAP sensing may not be reliable. In some examples, in response to an indication of noise from noise sensing circuitry 207, processing circuitry 210 may reject a request from a patient programmer to adjust stimulation parameters. For example, processing circuitry 210 may reject patient programmer requests to increase stimulation amplitude to avoid possible patient discomfort when the noise source is removed.

In some examples, one or more of electrodes 232 and 234 are suitable for sensing one or more ECAPs. For instance, electrodes 232 and 234 may sense the voltage amplitude of a portion of the ECAP signals, where the sensed voltage amplitude is a characteristic of the ECAP signal.

In some examples, one or more of electrodes 232 and 234 are suitable for sensing stimulation signals. For instance, electrodes 232 and 234 may sense the voltage amplitude of a portion of the stimulation signals, where the sensed voltage amplitude is a characteristic of the stimulation signals. In some examples, one or more of electrodes 232 and 234 may sense a stimulation signal in response to one or more of electrodes 232 and 234 delivering a stimulation pulse to target tissue of patient 105. In some examples, the one or more of electrodes 232 and 234 which sense the stimulation signal are not the same as the one or more of electrodes 232 and 234 which deliver the stimulation pulse.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. As discussed above, storage device 212 is configured to store therapy stimulation programs 214, test stimulation programs 216, and target values 218. In some examples, processing circuitry 210 may implement the closed loop policy based on an algorithm stored at storage device 212.

In some examples, stimulation generation circuitry 202 may be configured to deliver electrical stimulation therapy to patient 105. In some examples, the electrical stimulation therapy may include a plurality of informed pulses. Additionally, stimulation generation circuitry 202 may be configured to deliver a plurality of control pulses, where the plurality of control pulses is interleaved with at least some informed pulses of the plurality of informed pulses. Stimulation generation circuitry may deliver the plurality of informed pulses and the plurality of control pulses to target tissue (e.g., spinal cord 120) of patient 105 via electrodes 232, 234 of leads 230. By delivering such informed pulses and control pulses, stimulation generation circuitry 202 may cause IMD 200 to sense stimulation signals that are indicative of the delivered pulses Additionally, or alternatively, stimulation generation circuitry 202 may deliver control pulses that evoke detectable responsive ECAPs in the target tissue, the responsive ECAPs propagating through the target tissue before arriving back at electrodes 232, 234. Stimulation signals or ECAPs caused by or elicited by informed pulses may not be detectable by IMD 200. In some examples, a different combination of electrodes 232, 234 may sense responsive ECAPs and/or responsive stimulation signals than a combination of electrodes 232, 234 that delivers informed pulses and a combination of electrodes 232, 234 that delivers control pulses. Sensing circuitry 206 may be configured to detect the responsive ECAPs and/or the responsive stimulation signals via electrodes 232, 234 and leads 230. In other examples, stimulation generation circuitry 202 may be configured to deliver a plurality of control pulses, without any informed pulses, when control pulses also provide or contribute to a therapeutic effect for the patient.

Processing circuitry 210 may, in some cases, direct sensing circuitry 206 to continuously monitor for ECAPs and stimulation signals. In other cases, processing circuitry 210 may direct sensing circuitry 206 to monitor for ECAPs and stimulation signals based on signals from sensor(s) 222. For example, processing circuitry 210 may activate sensing circuitry 206 based on an activity level of patient 105 exceeding an activity level threshold (e.g., acceleration sensor 223 rises above a threshold). Activating and deactivating sensing circuitry 206 may, in some examples, extend a battery life of power source 224.

Processing circuitry 210 may determine whether electrical stimulation therapy delivered to target tissue of patient 105 via electrodes 232, 234 elicits enough detectable ECAPs for processing circuitry 210 to determine therapy based on one or more characteristics of the respective detectible ECAPs. It may be beneficial for processing circuitry 210 to determine therapy based on characteristics of detectible ECAPs rather than characteristics of detectible stimulation signals, if possible. However, if not enough responsive ECAPs are detectible by sensing circuitry 206, it may be beneficial for processing circuitry 210 to determine therapy based on one or more characteristics of respective stimulation signals, which are often still detectible even when some or all of elicited ECAPs are not detectible in response to a stimulation pulse. In addition, sensing circuitry 206 may still detect stimulation signals when the delivered stimulation pulses were insufficient to elicit a detectable ECAP signal (e.g., when the stimulation pulses are configured to be sub-threshold pulses).

In one example, to determine if the electrical stimulation therapy elicits enough detectible ECAPs, processing circuitry 210 is configured to perform a test to determine whether the plurality of pulses of the electrical stimulation therapy elicit greater than a threshold ratio of detectible ECAPs. For example, to perform the test, processing circuitry 210 may identify a set of ECAPs elicited by a sequence of consecutive pulses of the plurality of pulses. Subsequently, processing circuitry 210 may calculate a ratio of the set of ECAPs to the sequence of consecutive pulses. For example, processing circuitry 210 may first determine a number of ECAPs of the set of ECAPs and a number of pulses of the sequence of consecutive pulses, and then calculate a ratio of the number of ECAPs to the number of pulses.

There may be examples in which a particular one or more stimulation pulses of the sequence of consecutive pulses might not elicit ECAPs that are detectible by sensing circuitry 206, but another one or more stimulation pulses of the sequence of consecutive pulses do elicit ECAPs that are detectible by sensing circuitry 206. In such cases, processing circuitry 210 may be configured to determine therapy based on one or more characteristics of the detectible ECAPs rather than determine therapy based on one or more characteristics of detectible stimulation signals. In some examples, processing circuitry 210 may determine whether the ratio of detectible ECAPs to stimulation pulses is greater than the threshold ratio. In one or more cases where the ratio is greater than the threshold ratio, processing circuitry 210 may determine therapy based on characteristics of the detectible ECAPs. In one or more cases where the ratio is not greater than the threshold ratio, processing circuitry 210 may determine therapy based on characteristics of the detectible stimulation signals.

In some examples, responsive to determining that a plurality of pulses elicit greater than a threshold ratio of detectible ECAPs, processing circuitry 210 is configured to set, based on one or more characteristics of an ECAP, one or more parameters which at least partially define the one or more pulses deliverable by stimulation generation circuitry 202 after a stimulation pulse which elicits the respective ECAP. In some examples, responsive to determining that a plurality of pulses do not elicit greater than a threshold ratio of detectible ECAPs, processing circuitry 210 is configured to set, based on one or more characteristics of a stimulation signal, one or more parameters which at least partially define the one or more pulses deliverable by stimulation generation circuitry 202 after a stimulation pulse which elicits the respective stimulation signal. In some examples, processing circuitry 210 may set one or more parameters which at least partially define the one or more pulses deliverable by stimulation generation circuitry 202 based on a combination of characteristics of one or more detectable ECAPs and characteristics of one or more detectible stimulation signals.

Stimulation generation circuitry 202 may be configured to deliver one or more stimulation pulses, at least one of which may cause sensing circuitry 206 to sense a stimulation signal in response to the delivery of the respective pulse. In some examples, to sense a stimulation signal, sensing circuitry 206 may detect, via any one or combination of electrodes 232, 234, one or more electrical signals which are generated by stimulation generation circuitry 202 and delivered to patient 105 via any one or combination of electrodes 232, 234. In some examples, stimulation signals may include information which is useful for determining one or more parameters of upcoming therapy pulses generated by stimulation generation circuitry 202. For example, information included by a stimulation signal may include one or more characteristics which indicate an efficacy of therapy delivered to patient 105 via electrodes 232, 234. In some cases, the one or more characteristics may reflect a separation between one or more of electrodes 232, 234 and target tissue of patient 105 (e.g., spinal cord 120). Such a distance between electrodes 232, 234 and spinal cord 120 may be relevant to determining therapy since a smaller intensity (e.g., amplitude and/or pulse length) of therapy pulses is required to stimulate a nerve if electrodes 232, 234 move closer to spinal cord 120 and vice versa.

Determining therapy based on one or more stimulation signals may, in some cases, depend on a posture of patient 105. For example, processing circuitry 210 may be configured to determine a posture of patient 105 based on an acceleration signal generated by acceleration sensor 223. In some examples, the accelerometer signal includes a vertical component, a lateral component, and a frontal component corresponding to a vertical axis, a lateral axis, and a frontal axis, respectively. In this way, the accelerometer signal represents a three-dimensional measurement of acceleration. It may be beneficial for processing circuitry 210 to analyze one or more of the vertical axes, the lateral axis, and the frontal axis in order to determine a posture of patient 105.

In some examples, acceleration sensor 223 is configured to generate an accelerometer signal. Processing circuitry 210 is configured to identify, based on the accelerometer signal, a posture of a set of postures which patient 105 is occupying. The set of postures may include, for example, a standing posture, a sitting posture, a supine posture, a prone posture, a side-lying posture, or any combination thereof. In some examples, expected parameter values of the accelerometer signal corresponding to each posture of the set of postures are stored in storage device 212. Subsequently, processing circuitry 210 may select, based on the identified posture, a target stimulation signal value (e.g., a target range of characteristic values) for a stimulation signal sensed by IMD 200 in response to a delivery of a corresponding stimulation pulses. For example, if stimulation generation circuitry 202 generates a stimulation pulse having a stimulation amplitude and delivers the stimulation pulse to target tissue of patient 105 via one or a combination of electrodes 232, 234, processing circuitry 210 may select, based on a posture of patient 105 during the delivery of the stimulation pulse, a target range for a characteristic of the resulting stimulation signal sensed by sensing circuitry 106. Subsequently, processing circuitry 210 may determine whether to change one or more parameters of therapy stimulation programs 314 and/or test stimulation programs 216 based on whether the characteristic value is within the target range of characteristic values selected based on the posture of patient 105.

In some examples, processing circuitry 210 is configured to identify, based on the accelerometer signal, a posture of a set of postures which patient 105 is occupying while a stimulation pulse is delivered and identify an amplitude of the stimulation pulse. Subsequently, processing circuitry 210 may select a target range of characteristic values for a characteristic of a stimulation signal sensed by sensing circuitry 206 in response to the delivery of the stimulation pulse based on both of the posture of patient 105 and the amplitude of the stimulation pulse. For example, target values 218 may include a respective transfer function corresponding to each posture of the set of postures. Each transfer function represents a relationship (e.g., a linear relationship) between the amplitude of a stimulation pulse and the target stimulation signal value (e.g., a target range of characteristic values) for a stimulation signal sensed by IMD 200 in response to the delivery of the stimulation pulse. As such, processing circuitry 210 may, when evaluating whether to change one or more parameters of upcoming stimulation pulses, first select a transfer function corresponding to a present stimulation pulse and subsequently select a target range of characteristics based on the amplitude of the present stimulation pulse, but this is not required. Processing circuitry 210 may first analyze the amplitude of the stimulation pulse and subsequently determine the posture of patient 105, in some cases.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

Figure 3:
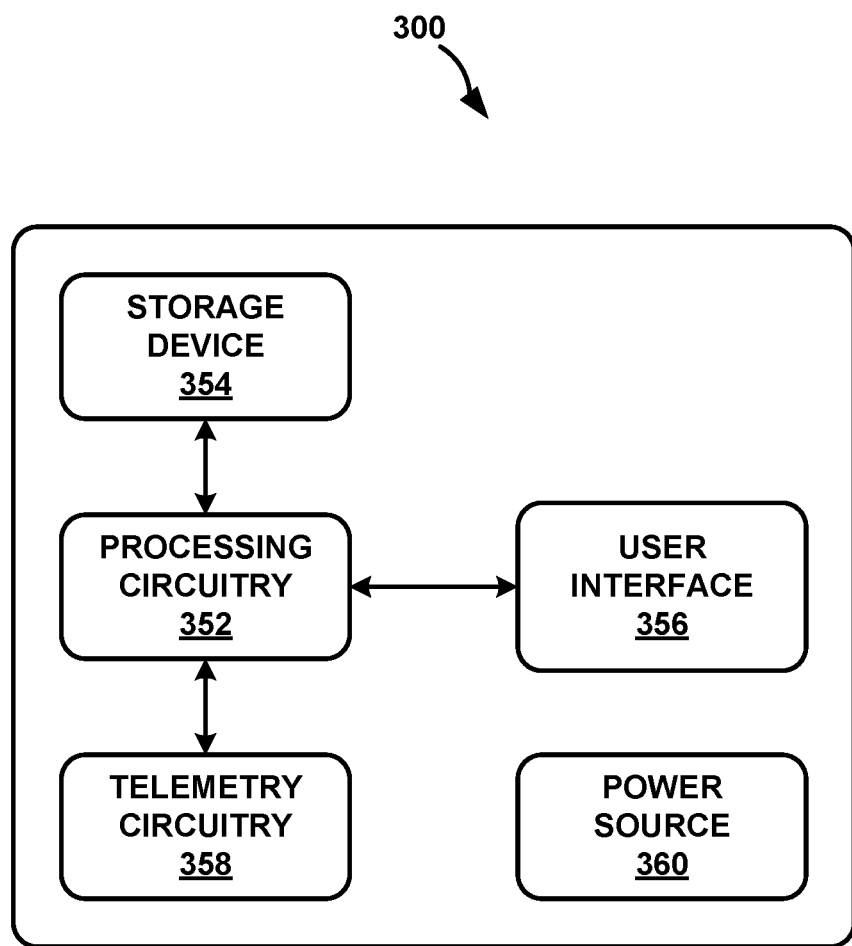
FIG. 3 is a block diagram illustrating an example configuration of components of the external programmer of FIG. 1, in accordance with one or more techniques of this disclosure.

FIG. 3 is a block diagram illustrating an example configuration of components of external programmer 300, in accordance with one or more techniques of this disclosure. External programmer 300 may be an example of external programmer 150 of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, telemetry circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any arrangement of hardware, alone or in combination with software and/or firmware, configured to perform the techniques attributed to external programmer 300, and processing circuitry 352, user interface 356, and telemetry circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory, select a spatial electrode movement pattern, or receive a user input and send a corresponding command to IMD 200, or instructions for any other functionality. In addition, storage device 354 may include a plurality of programs, where each program includes a parameter set that defines stimulation pulses, such as control pulses and/or informed pulses. Storage device 354 may also store data received from a medical device (e.g., IMD 110). For example, storage device 354 may store ECAP related data recorded at a sensing module of the medical device, and storage device 354 may also store data from one or more sensors of the medical device.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation, identified patient behaviors, sensed patient parameter values, patient behavior criteria, or any other such information. User interface 356 may also receive user input via user interface 356. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation. For example, the input may request an increase or decrease to stimulation intensity (e.g., amplitude, pulse width, or frequency). Programmer 300 can then transmit these requests to IMD 200. Programmer 300 may receive, and transmit, the input requesting changes to one or more parameter values during closed-loop stimulation in some examples.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameter values to IMD 110 for delivery of electrical stimulation therapy.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external programmer 300 provides visual, audible, and/or tactile notifications that indicate there are new instructions. External programmer 300 requires receiving user input acknowledging that the instructions have been completed in some examples.

According to the techniques of the disclosure, user interface 356 of external programmer 300 receives an indication from a clinician instructing a processor of the medical device to update one or more therapy stimulation programs or to update one or more test stimulation programs. Updating therapy stimulation programs and test stimulation programs may include changing one or more parameters of the stimulation pulses delivered by the medical device according to the programs, such as amplitude, pulse width, frequency, and pulse shape of the informed pulses and/or control pulses. User interface 356 may also receive instructions from the clinician commanding any electrical stimulation, including control pulses and/or informed pulses to commence or to cease.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

Figure 4:
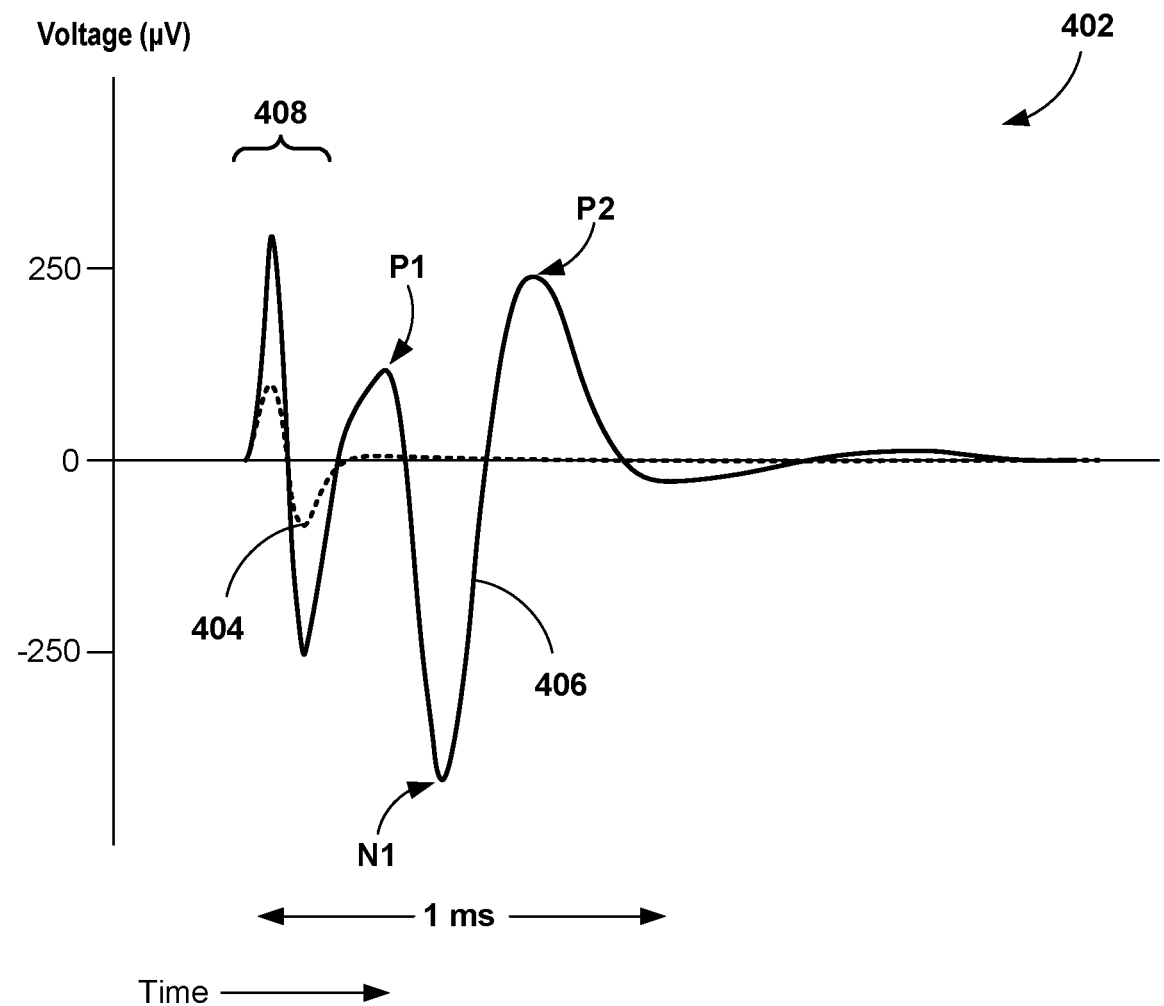
FIG. 4 is a graph of example evoked compound action potentials (ECAPs) sensed for respective stimulation pulses, in accordance with one or more techniques of this disclosure.

FIG. 4 is a graph 402 of example evoked compound action potentials (ECAPs) sensed for respective stimulation pulses, in accordance with one or more techniques of this disclosure. As shown in FIG. 4, graph 402 shows example ECAP signal 404 (dotted line) and ECAP signal 406 (solid line). In some examples, each of ECAP signals 404 and 406 are sensed from stimulation pulses (e.g., a control pulse) that were delivered from a guarded cathode, where the stimulation pulses are bi-phasic pulses including an interphase interval between each positive and negative phase of the pulse. In some such examples, the guarded cathode includes stimulation electrodes located at the end of an 8-electrode lead (e.g., leads 130 of FIG. 1) while two sensing electrodes are provided at the other end of the 8-electrode lead. ECAP signal 404 illustrates the voltage amplitude sensed as a result from a sub-detection threshold stimulation pulse, or a stimulation pulse which results in no detectable ECAP. It is noted that monophasic, tri-phasic, or pulses with another quantity of phases may be in other examples.

Peaks 408 of ECAP signal 404 are detected and represent stimulation signals of the delivered stimulation pulse. However, no propagating signal is detected after the stimulation signal in ECAP signal 404 because the stimulation pulse had an intensity (e.g., an amplitude and/or pulse width) that was "sub-threshold" or below a detection threshold (e.g., a sub-detection threshold) and/or below a propagation threshold (e.g., a sub-propagation threshold). In other examples, sensing circuitry, such as sensing circuitry 206 described above in relation to FIG. 2, may measure other signal features, such as features based on a derivative of the sensed signal, slope, linearity, and so on. The processing circuitry may react to the peaks 408 of ECAP signal 404, or any other measurable or calculated signal feature.

In contrast to ECAP signal 404, ECAP signal 406 represents the voltage amplitude detected from a supra-detection stimulation threshold stimulation pulse. Peaks 408 of ECAP signal 406 are detected and represent stimulation signals of the delivered stimulation pulse. After peaks 408, ECAP signal 406 also includes peaks P1, N1, and P2, which are three typical peaks representative of propagating action potentials from an ECAP. The example duration of the stimulation signal and peaks P1, N1, and P2 is approximately 1 millisecond (ms).

When detecting the ECAP of ECAP signal 406, different characteristics may be identified. For example, the characteristic of the ECAP may be the amplitude between N1 and P2. This N1-P2 amplitude may be easily detectable even if the stimulation signal impinges on P1, a relatively large signal, and the N1-P2 amplitude may be minimally affected by electronic drift in the signal. In other examples, the characteristic of the ECAP used to control subsequent stimulation pulses (e.g., control pulses and/or informed pulses) may be an amplitude of P1, N1, or P2 with respect to neutral or zero voltage. In some examples, the characteristic of the ECAP used to control subsequent stimulation pulses is a sum of two or more of peaks P1, N1, or P2. In other examples, the characteristic of ECAP signal 406 may be the area under one or more of peaks P1, N1, and/or P2. In other examples, the characteristic of the ECAP may be a ratio of one of peaks P1, N1, or P2 to another one of the peaks. In some examples, the characteristic of the ECAP is a slope between two points in the ECAP signal, such as the slope between N1 and P2. In other examples, the characteristic of the ECAP may be the time between two points of the ECAP, such as the time between N1 and P2.

The time between when the stimulation pulse is delivered and a point in the ECAP signal may be referred to as a latency of the ECAP and may indicate the types of fibers being captured by the stimulation pulse (e.g., a control pulse). ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Latency may also refer to the time between an electrical feature is detected at one electrode and then detected again at a different electrode. This time, or latency, is inversely proportional to the conduction velocity of the nerve fibers. Other characteristics of the ECAP signal may be used in other examples.

The amplitude of the ECAP signal increases with increased amplitude of the stimulation pulse, as long as the pulse amplitude is greater than threshold such that nerves depolarize and propagate the signal. The target ECAP characteristic (e.g., the target ECAP amplitude) may be determined from the ECAP signal detected from a stimulation pulse (or a control pulse) when informed pulses are determined to deliver effective therapy to patient 105. The ECAP signal thus is representative of the distance between the stimulation electrodes and the nerves appropriate for the stimulation parameter values of the informed pulses delivered at that time. Therefore, IMD 110 may attempt to use detected changes to the measured ECAP characteristic value to change therapy pulse parameter values and maintain the target ECAP characteristic value during therapy pulse delivery.

Figure 5:
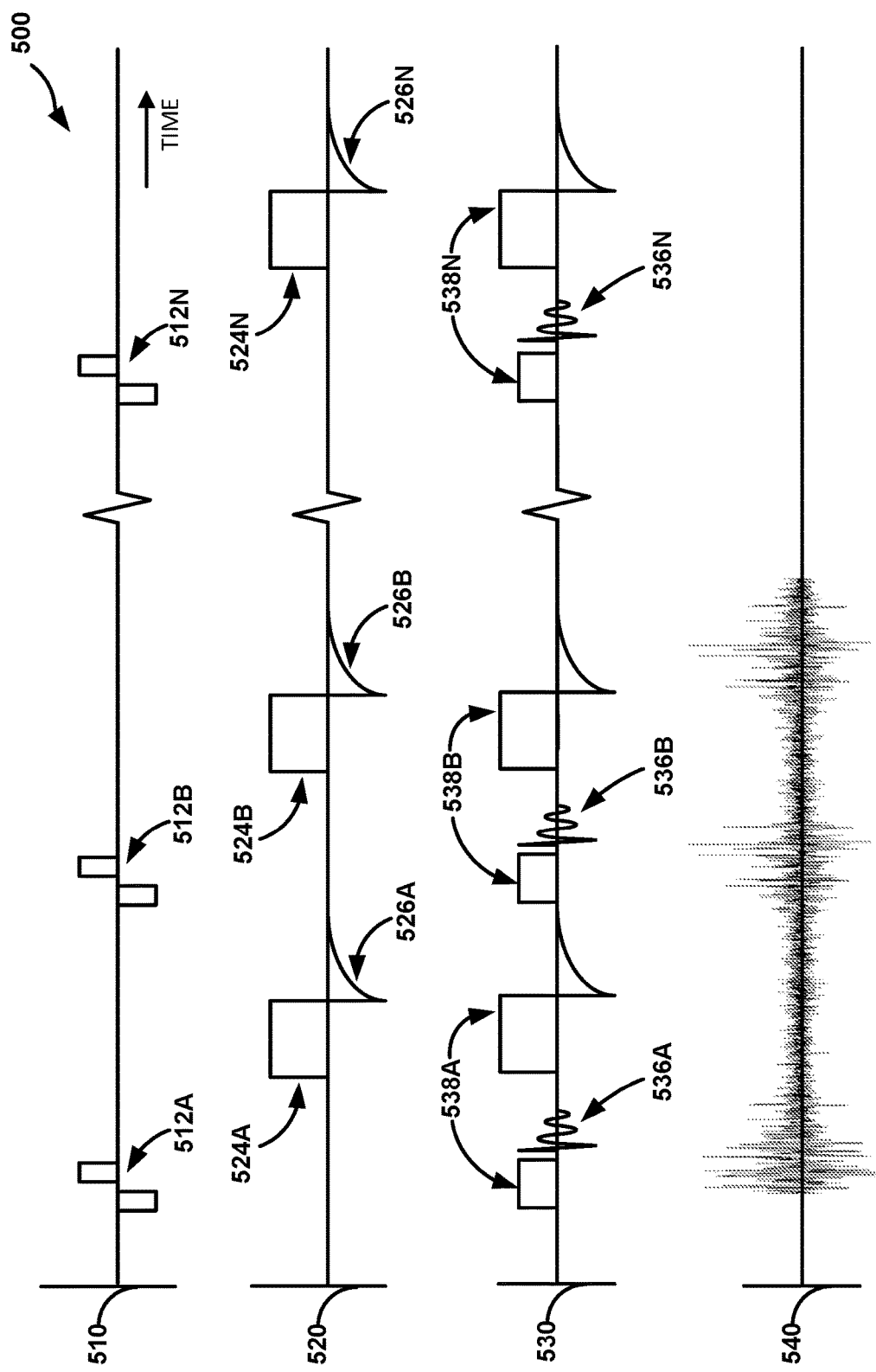
FIG. 5 is an example timing diagram illustrating an example of electrical stimulation pulses, respective stimulation signals, and respective sensed ECAPs, in accordance with one or more techniques of this disclosure.

FIG. 5 is a timing diagram 500 illustrating one example of electrical stimulation pulses, respective stimulation signals, and respective sensed ECAPs, in accordance with one or more techniques of this disclosure. For convenience, FIG. 5 is described with reference to IMD 200 of FIG. 2. As illustrated, timing diagram 500 includes first channel 510, a plurality of control pulses 512A-512N (collectively "control pulses 512"), second channel 520, a plurality of informed pulses 524A-524N (collectively "informed pulses 524") including passive recharge phases 526A-526N (collectively "passive recharge phases 526"), third channel 530, a plurality of respective ECAPs 536A-536N (collectively "ECAPs 536"), and a plurality of stimulation signals 538A-538N (collectively "stimulation signals 538").

In some examples, external noise from a fourth channel 540 may interfere with the operation of an IMD, such as IMD 200 of FIG. 2 and IMD 110 of FIG. 1. Noise on channel 540 may couple to any of leads 230, electrodes 232 and 234, and in some examples couple to the IMD. Sensing circuitry 206 may sense noise from channel 540. Some of the noise may not be canceled or excluded by the filter circuitry of sensing circuitry 206, and processing circuitry 210 may interpret noise from channel 540 as a received ECAP signal. Sources of noise may include nearby electric motors, microwave ovens, machinery, computing devices, recharging circuits, generators, and so on. As one example, patient 105 may be seated in a powered massage chair that may include motors and other circuitry. Noise generated by the massage chair circuitry may couple into sensing circuitry 206. Also, pressure rollers in the massage chair may press against leads 230 and change the position of the lead with respect to the target tissue of patient 105. As shown in FIG. 5, the noise signal on channel 540 may vary in amplitude, frequency, and other characteristics, and may start and stop at different times during operation of IMD 200.

First channel 510 is a time/voltage (and/or current) graph indicating the voltage (or current) of at least one electrode of electrodes 232, 234. In one example, the stimulation electrodes of first channel 510 may be located on the opposite side of the lead as the sensing electrodes of third channel 530. Control pulses 512 may be electrical pulses delivered to the spinal cord of the patient by at least one of electrodes 232, 234, and control pulses 512 may be balanced biphasic square pulses with an interphase interval. In other words, each of control pulses 512 are shown with a negative phase and a positive phase separated by an interphase interval. For example, a control pulse 512 may have a negative voltage for the same amount of time that it has a positive voltage. It is noted that the negative voltage phase may be before or after the positive voltage phase. Control pulses 512 may be delivered according to test stimulation programs 216 stored in storage device 212 of IMD 200, and test stimulation programs 216 may be updated according to user input via an external programmer and/or may be updated according to a signal from sensor(s) 222. In one example, control pulses 512 may have a pulse width of less than approximately 300 microseconds (e.g., the total time of the positive phase, the negative phase, and the interphase interval is less than 300 microseconds). In another example, control pulses 512 may have a pulse width of approximately 100 µs for each phase of the bi-phasic pulse. As illustrated in FIG. 5, control pulses 512 may be delivered via first channel 510. Delivery of control pulses 512 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 520 is a time/voltage (and/or current) graph indicating the voltage (or current) of at least one electrode of electrodes 232, 234 for the informed pulses. In one example, the electrodes of second channel 520 may partially or fully share common electrodes with the electrodes of first channel 510 and third channel 530. Informed pulses 524 may also be delivered by the same leads 230 that are configured to deliver control pulses 512. Informed pulses 524 may be interleaved with control pulses 512, such that the two types of pulses are not delivered during overlapping periods of time. However, informed pulses 524 may or may not be delivered by exactly the same electrodes that deliver control pulses 512. Informed pulses 524 may be monophasic pulses with pulse widths of greater than approximately 300 µs and less than approximately 1000 µs. In fact, informed pulses 524 may be configured to have longer pulse widths than control pulses 512. As illustrated in FIG. 5, informed pulses 524 may be delivered on second channel 520.

Informed pulses 524 may be configured for passive recharge. For example, each informed pulse 524 may be followed by a passive recharge phase 526 to equalize charge on the stimulation electrodes. Unlike a pulse configured for active recharge, where remaining charge on the tissue following a stimulation pulse is instantly removed from the tissue by an opposite applied charge, passive recharge allows tissue to naturally discharge to some reference voltage (e.g., ground or a rail voltage) following the termination of the therapy pulse. In some examples, the electrodes of the medical device may be grounded at the medical device body. In this case, following the termination of informed pulse 524, the charge on the tissue surrounding the electrodes may dissipate to the medical device, creating a rapid decay of the remaining charge at the tissue following the termination of the pulse. This rapid decay is illustrated in passive recharge phases 526. Passive recharge phase 526 may have a duration in addition to the pulse width of the preceding informed pulse 524. In other examples (not pictured in FIG. 5), informed pulses 524 may be bi-phasic pulses having a positive and negative phase (and, in some examples, an interphase interval between each phase) which may be referred to as pulses including active recharge. An informed pulse that is a bi-phasic pulse may or may not have a following passive recharge phase.

Third channel 530 is a time/voltage (and/or current) graph indicating the voltage (or current) of at least one electrode of electrodes 232, 234. In one example, the electrodes of third channel 530 may be located on the opposite side of the lead as the electrodes of first channel 510. ECAPs 536 may be sensed at electrodes 232, 234 from the spinal cord of the patient in response to control pulses 512. ECAPs 536 are electrical signals which may propagate along a nerve away from the origination of control pulses 512. In one example, ECAPs 536 are sensed by different electrodes than the electrodes used to deliver control pulses 512. As illustrated in FIG. 5, ECAPs 536 may be recorded on third channel 530.

Stimulation signals 538A, 538B, and 538N may be sensed by leads 230 and may be sensed during the same period of time as the delivery of control pulses 512 and informed pulses 524. Since the stimulation signals may have a greater amplitude and intensity than ECAPs 536, any ECAPs arriving at IMD 200 during the occurrence of stimulation signals 538 may not be adequately sensed by sensing circuitry 206 of IMD 200. However, ECAPs 536 may be sufficiently sensed by sensing circuitry 206 because each ECAP 536 falls after the completion of each a control pulse 512 and before the delivery of the next informed pulse 524. As illustrated in FIG. 5, stimulation signals 538 and ECAPs 536 may be recorded on channel 530. In some examples, noise from channel 540 may be interpreted as ECAPs 536. In other words, noise from channel 540 may cause the IMD to interpret that a value of a characteristic of one or more sensed ECAPs 536 is outside of a predetermined range. As described above in relation to FIGS. 1 and 2, a closed loop algorithm executed by processing circuitry on either IMD 110, IMD 200 or external programmer 150 may adjust the one or more parameters defining the electrical stimulation therapy based on analysis of the sensed signals. For example, the processing circuitry may compare a characteristic value of the stimulation signal to the respective target range of characteristic values, and in response to the comparison, the closed loop algorithm executed by the processing circuitry may adjust one or more parameters that define the electrical stimulation pulses delivered to patient 105. In some examples, based on the closed loop algorithm, processing circuitry 210 may cause stimulation generation circuitry 202 to adjust a first set of parameter values for the plurality of pulses to a second set of parameter values. As one example, stimulation generation circuitry 202 may reduce an amplitude of current for a control pulse or for an informed pulse, or both, from a first current amplitude to a second current amplitude. In other examples, stimulation generation circuitry 202 may also adjust one or more of pulse width, voltage amplitude or other parameters in the set of parameters from a first value to a second value.

As described above in relation to FIG. 2, processing circuitry 210 may receive commands from a patient programmer, e.g. external programmer 150, when the patient wishes to terminate or change electrical stimulation therapy. In some examples, the medical device may be adapting to changes in the patient's physiological signals, such as when the patient changes posture, activity level. The patient may request an increase in stimulation (e.g., increase the value of the amplitude parameter) while IMD 200 is decreasing stimulation due to elevated characteristic values of the sensed ECAP signals (which may be due to noise). In other examples, noise from channel 540 may be sensed as ECAPs 536 exceeding an upper limit of a predetermined range and the closed loop algorithm of IMD 200 may respond by decreasing a parameter value to reduce the sensed ECAP. To avoid the risk of patient discomfort when the noise is removed (or no longer present), or when the physiological signals change again, in some examples, processing circuitry 210 may prevent stimulation generation circuitry 202 from responding to the commands from the patient programmer when processing circuitry 210 determines that stimulation therapy parameters, e.g. informed pulse amplitude, is outside of a predetermined pulse amplitude range of a default pulse amplitude. For example, processing circuitry 210 may reject a user command to increase amplitude of stimulation when the closed loop algorithm is reducing amplitude in response to elevated characteristics of the ECAP signal.

In some examples, when noise from channel 540 is sensed as ECAPs 536 exceeding an upper limit of a predetermined range and the closed loop algorithm of IMD 200 responds by decreasing a parameter value to reduce the sensed ECAP, processing circuitry may determine that the sensed ECAP is distorted by noise. For example, a control pulse or an informed pulse may have a minimum parameter value, such as a pulse amplitude of zero or pulse width of zero. When the closed loop algorithm adjusts the parameter to the minimum value, and the ECAP sensed by sensing circuitry 206 is still above the upper limit, processing circuitry 210 may determine that noise coupled from channel 540 may be causing the high value of the sensed ECAP. In some examples, processing circuitry 210 may disable the closed loop algorithm when processing circuitry determines that the sensed ECAPs 536 may be influenced by noise coupled from channel 540. Processing circuitry 210 may execute a control policy to ramp the stimulation pulse parameter to a specified value, such as a default value, until processing circuitry 210 determines that the noise has diminished or been removed. In this manner, IMD 200 may avoid pulse stimulation parameter levels that may cause the patient to receive inappropriate stimulation (over or under stimulation) resulting in patient discomfort.

Figure 6:
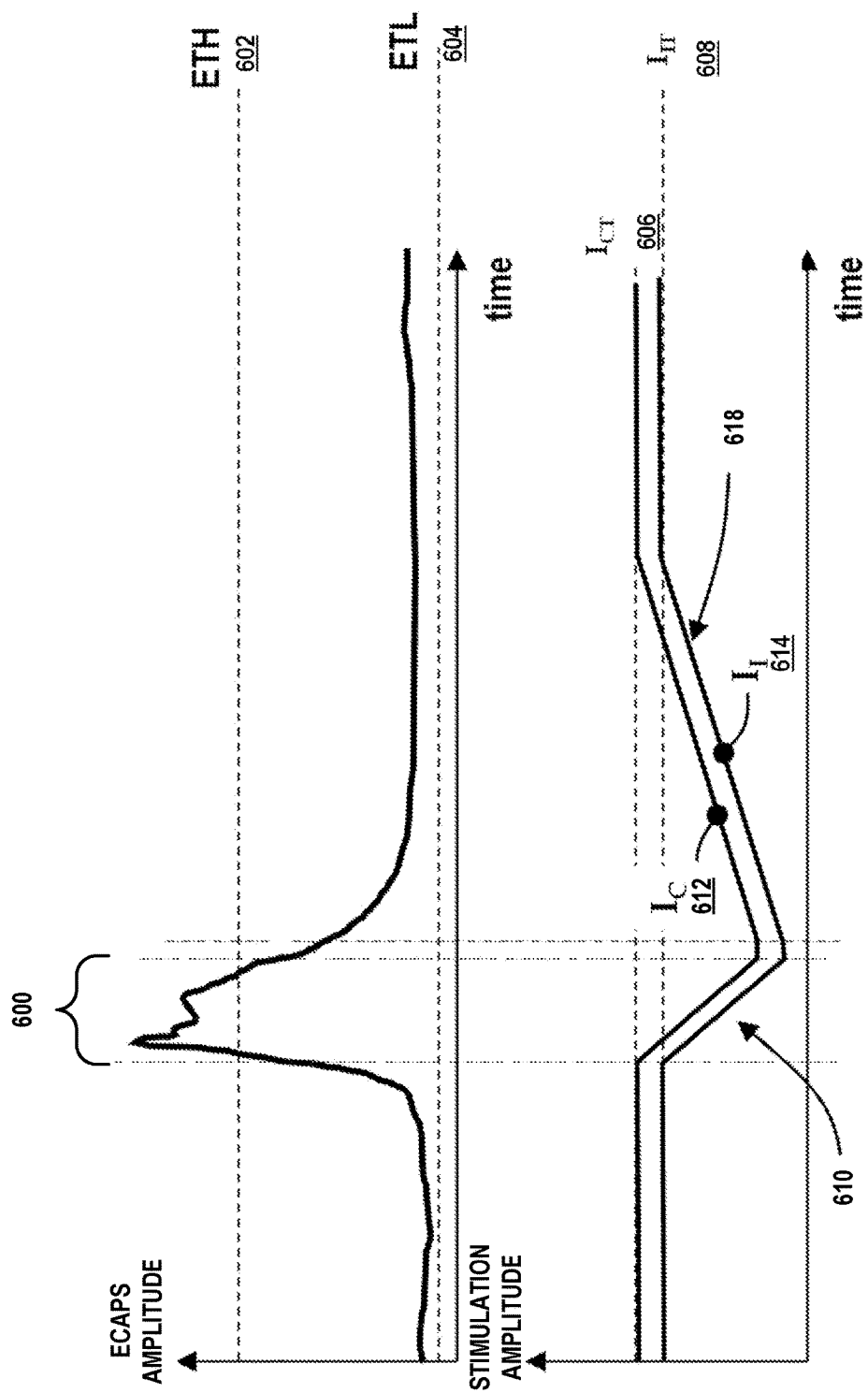
FIG. 6 is a timing diagram illustrating an example closed loop response to a sensed ECAP that is outside of a predetermined range, in accordance with one or more techniques of this disclosure.

FIG. 6 is a timing diagram illustrating a closed loop response to a sensed ECAP that is outside of a predetermined range, in accordance with one or more techniques of this disclosure. As described above, in this disclosure the closed loop algorithm may be referred to as ECAP responsive stimulation or ERS. The example of FIGS. 6-16 will be described in terms of FIG. 2, unless otherwise noted. Programming commands for ERS may be stored at storage device 212, e.g. at test stimulation programs 216.

Storage device 212 may store a predetermined range for one or more values of a characteristic of the sensed ECAP. In the example of FIG. 6, the predetermined range includes an ECAP high threshold (ETH 602) and an ECAP low threshold (ETL 604) for a sensed magnitude (voltage or current). Processing circuitry 210 may determine a value of a characteristic of the sensed ECAP (600) that is outside of a predetermined range, when the sensed ECAP signal exceeds the ECAP high threshold 602. In response, ERS may be configured to adjust a first set of parameter values for stimulation pulses delivered during the time the sensed ECAP exceeds ETH 602 to a second set of parameter values (610). In the example of FIG. 6, processing circuitry 210 may cause stimulation generation circuitry 202 to reduce the control pulse current amplitude Ic 612 from Ict 606 to a lower amplitude. Similarly, stimulation generation circuitry 202 may reduce informed pulse current amplitude Ii 614 from Iit 608 to a lower amplitude. In this disclosure, Ict 606 is the default control pulse current amplitude, and Iit 608 is the default informed pulse current amplitude. As described above in relation to FIGS. 1 and 2, current pulse amplitude is just one example of a parameter value that defines the stimulation pulse delivered by IMD 200. In other examples, stimulation generation circuitry 202 may adjust pulse width, voltage amplitude, pulse shape, frequency, and so on, based on commands from processing circuitry 210.

As the high sensed ECAP signal 600 falls below ETH 602 and back within the predetermined range, ERS, executed by processing circuitry 210, may increase control pulse current amplitude Ic 612 and informed pulse current amplitude Ii 614 back to the default values of Ict 606 and Iit 608 (618).

Figure 7:
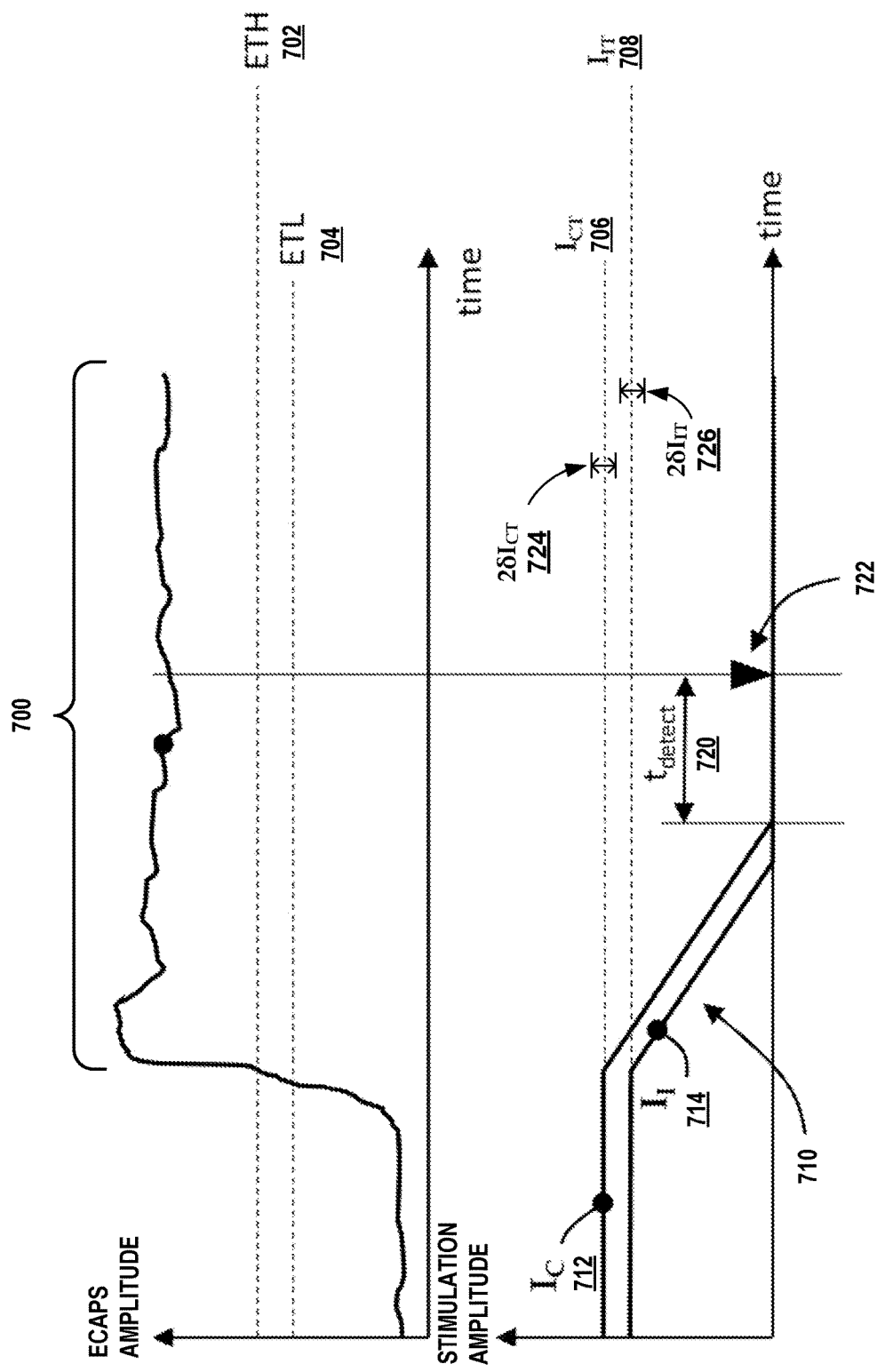
FIG. 7 is a timing diagram illustrating an example technique for suspending a closed loop algorithm, in accordance with one or more techniques of this disclosure.

FIG. 7 is a timing diagram illustrating suspending a closed loop algorithm, in accordance with one or more techniques of this disclosure. Similar to the example of FIG. 6, processing circuitry 210 may determine that the high sensed ECAP signal 700 exceeds ETH 702 and begin to decrease control pulse current amplitude Ic 712 from Ict 706 to a lower amplitude. Similarly, stimulation generation circuitry 202 may reduce informed pulse current amplitude Ii 714 from Iit 708 to a lower amplitude. However, in the example of FIG. 7, high sensed ECAP 700 persists, which may result in processing circuitry 210 adjusting control pulse current amplitude Ic 712 and/or informed pulse current amplitude Ii 714 to a minimum value, such as an amplitude of approximately zero amps (710). In response to adjusting the stimulation amplitude to the minimum value, processing circuitry 210 may start a noise detection timer, Tdetect 720. In the example of FIG. 7, in response to determining that Tdetect 720 has expired and the sensed ECAP 700 still exceed ETH 702, processing circuitry 210 may disable the closed-loop algorithm (722).

As described above in relation to FIG. 5, processing circuitry 210 may also disable some requests from patient programmer 150 while a control policy is adjusting stimulation parameters. One of several possible techniques to determine whether a control policy is adjusting stimulation parameters is to determine whether control pulse current amplitude Ic 712 and/or informed pulse current amplitude Ii 714 is outside of a predetermined range from the default values Ict 706 and Iit 708. Other example techniques may include checking a flag stored in memory that processing circuitry 210 may set when adjusting stimulation parameters. For example, if the flag is cleared, processing circuitry 210 may allow requests from patient programmer 150 to adjust stimulation parameters. If the flag is set, processing circuitry 210 may allow requests to decrease stimulation, but reject requests to increase stimulation.

In the example of FIG. 7, the predetermined range from the default values may be a range (±δIct) about the controlled pulse default value i.e., 2δIct 724. Similarly, the predetermined range may be a range (±δIit) about the informed pulse default value, i.e., 2δIit 726. In other words, processing circuitry 210 may determine whether the set of parameter values for the electrical stimulation therapy control pulse current amplitude Ic 712 and/or informed pulse current amplitude Ii 714 is approximately equal to the default set of parameter values Ict 706 and Iit 708. Because the sensed ECAP 700 is high and ERS has caused Ic 712 and Ii 714 to decrease to minimum levels, processing circuitry would determine that Ic 712 and Ii 714 are outside the predetermined range, 2δIct 724 and 2δIit 726 respectively, from the default values Ict 706 and Iit 708, and therefore may disable patient programmer input from changing the stimulation pulse parameters.

Figure 8:
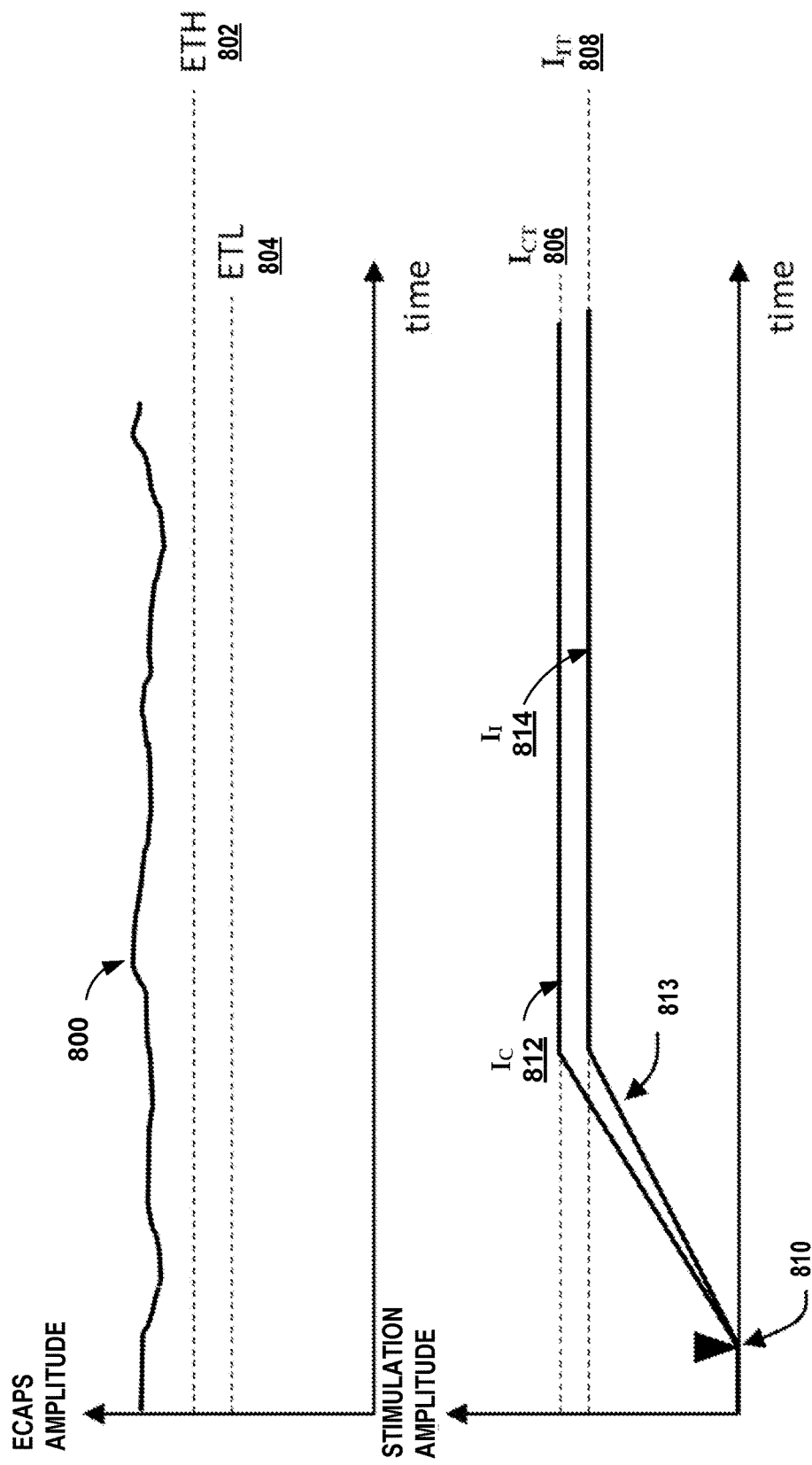
FIG. 8 is a timing diagram illustrating an example medical device providing electrical stimulation while suspending a closed loop algorithm, in accordance with one or more techniques of this disclosure.

FIG. 8 is a timing diagram illustrating a medical device providing electrical stimulation while suspending a closed loop algorithm, in accordance with one or more techniques of this disclosure. In the example of noise, e.g. from channel 540 of FIG. 5, causing sensed ECAP 800 to exceed ETH 802 for an extended period, the closed loop algorithm may decrease the stimulation pulses, e.g. as shown in FIG. 7, which may result in under stimulation for the patient. The patient, e.g. patient 105 of FIG. 1, may experience discomfort such as a return of pain symptoms, Parkinson's symptoms etc. as a result of the under stimulation caused by the presence of noise.

In the example of FIG. 8, in response to suspending ERS (810), processing circuitry 210 may cause stimulation generation circuitry 202 to increase the pulse parameter values of Ic 812 and Ii 814 back to the default values Ict 806 and Iit 808. In other words, in response to disabling the closed loop algorithm (810), the processing circuitry may adjust the informed pulse parameter values and the control pulse parameter values from the minimum of parameter values to the default set of parameter values (813). In this manner IMD 200 may continue to deliver therapy in the presence of noise. ERS may remain suspended and any sensed ECAP may be only monitored, but not affect the therapy delivery. Although the control pulse amplitude and informed pulse amplitude are shown as a continuous ramped back to their respective default levels, IMD 200 may use a step-wise ramp or immediate single jump back to their default levels in other examples.

In other examples, (not shown in FIG. 8), IMD 200 may ramp the parameter values, e.g. the stimulation levels of Ic 812 and Ii 814 to a value different from the default values Ict 806 and Iit 808. For example, IMD 200 may ramp the parameter values to a percentage of the default values Ict 806 and Iit 808, e.g. 70%, 75% or some other percentage. Returning to a sub-default level may provide an advantage by providing some stimulation for therapeutic purposes while avoiding possible overstimulating the patient if the patient is in an awkward posture where returning to the default level would overstimulate the target tissue, e.g. the spinal cord. In other words, returning to a sub-default may balance sufficient stimulation while lowering the risk of 'overstimulation' caused by patient posture or other reasons.

Figure 9:
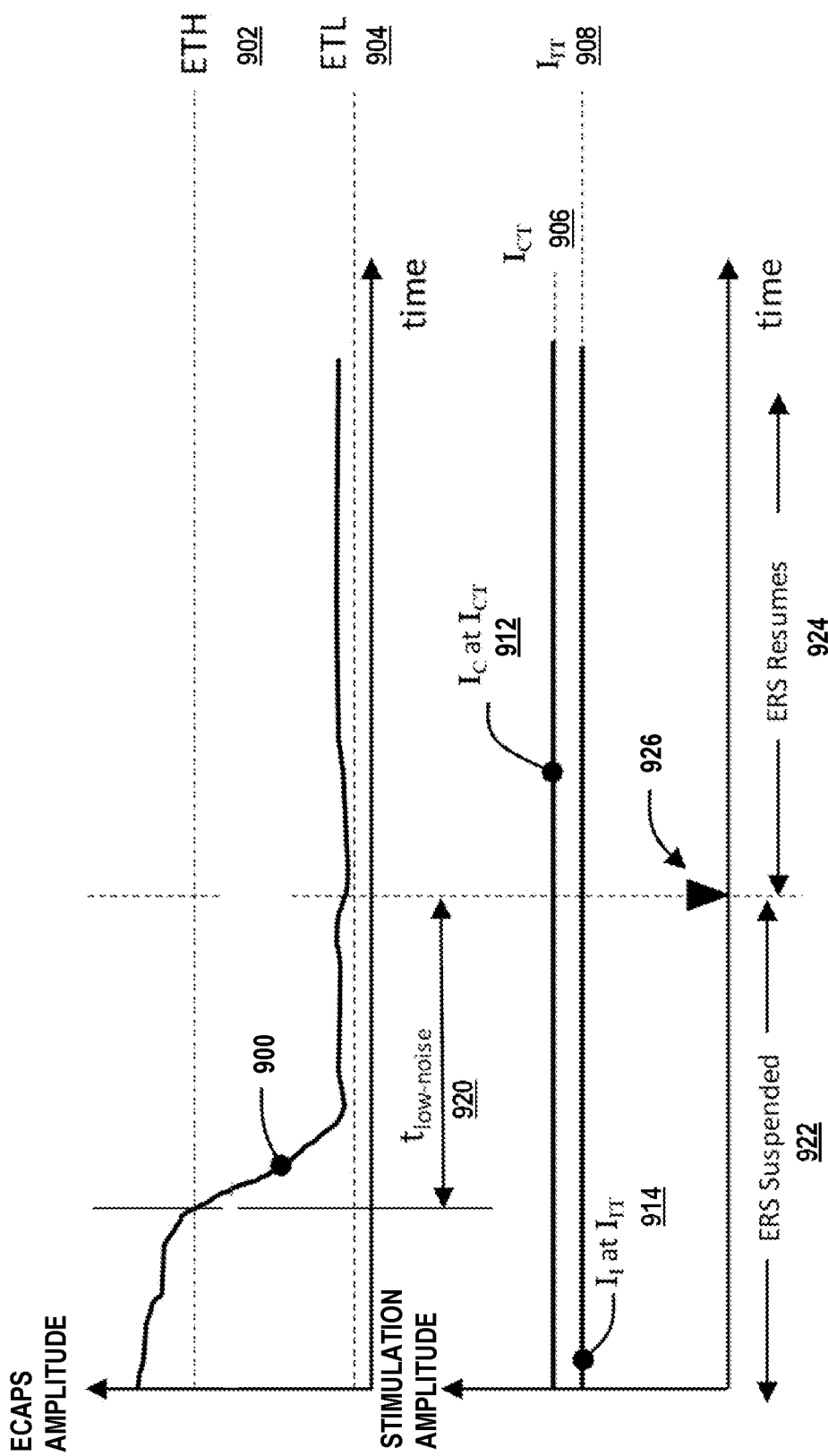
FIG. 9 is a timing diagram illustrating an example of recovering a suspended closed-loop algorithm, in accordance with one or more techniques of this disclosure.

FIG. 9 is a timing diagram illustrating an example of recovering a suspended closed-loop algorithm, in accordance with one or more techniques of this disclosure. As described above in relation to FIG. 8, processing circuitry 210 may cause Ic 912 and Ii 914 to increase back to the default values Ict 906 and Iit 908 to avoid under stimulation while noise may impact ECAP measurement. In the example of FIG. 9, while ERS is suspended 922, processing circuitry 210 may monitor ECAP signals from sensing circuitry 206 but make no adjustments to stimulation pulse parameters.

When the sensed ECAP falls back into the predetermined range, between ETH 902 and ETL 904, processing circuitry 210 may start a low-noise timer, $T_{low-noise}$ 920. In response to determining that low-noise timer 920 has expired, processing circuitry 210 may resume the closed-loop algorithm (924). In other words, when processing circuitry 210 detects that the noise has abated, e.g. ECAP 900 is less than ETH 902 for at least the duration of $T_{low-noise}$ 920, processing circuitry 210 may enable ERS. With ERS enabled, processing circuitry may cause stimulation generation circuitry 202 to adjust stimulation pulse parameters in response to changes in the sensed ECAP. Also, with Ic 912 and Ii 914 approximately equal to the default values Ict 906 and Iit 908, processing circuitry may respond to commands from patient programmer 150.

Figure 10:
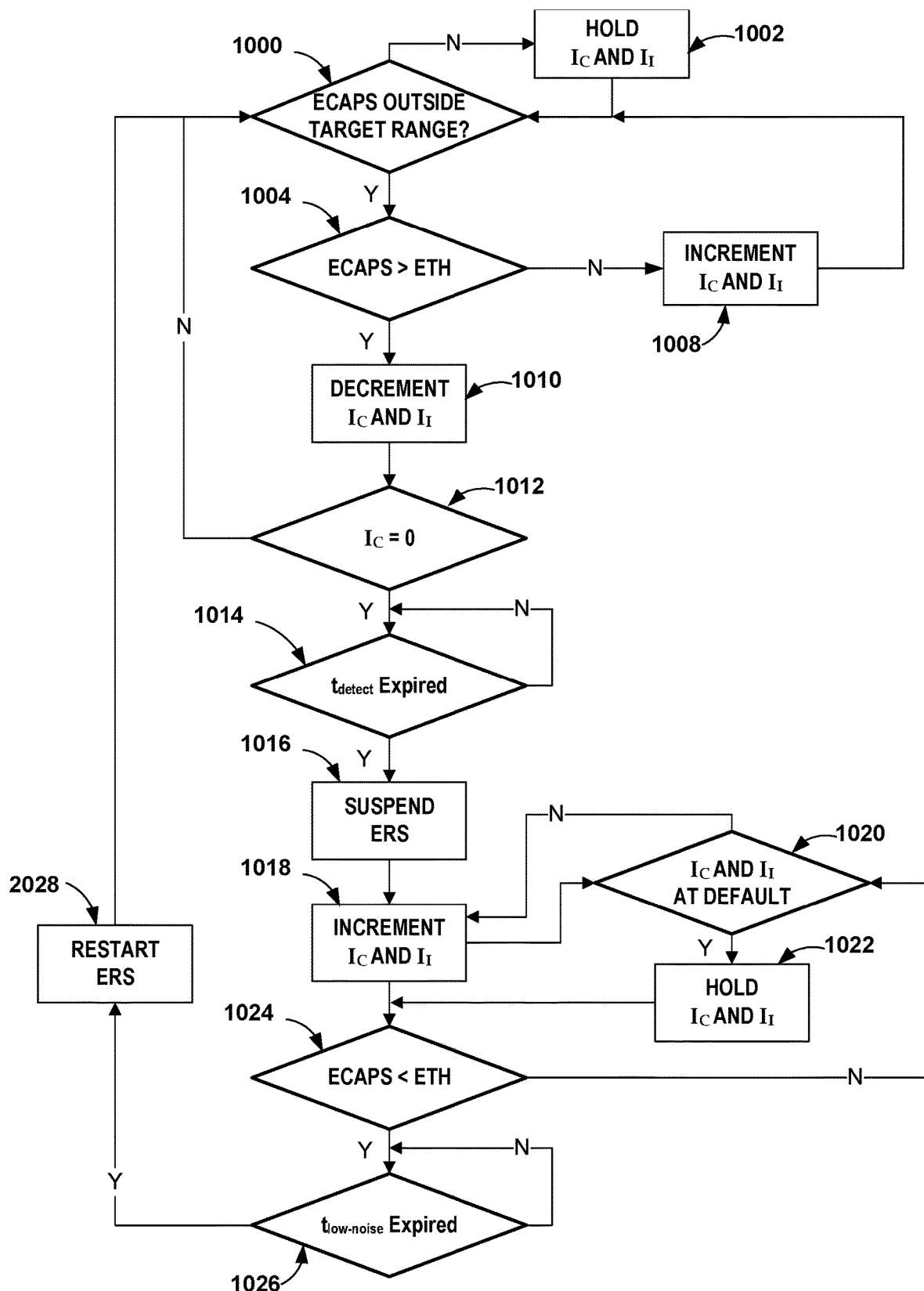
FIG. 10 is a flow diagram illustrating an example operation for suspending and recovering a suspended closed-loop algorithm, in accordance with one or more techniques of this disclosure.

FIG. 10 is a flow diagram illustrating an example operation for suspending and recovering a suspended closed-loop algorithm, in accordance with one or more techniques of this disclosure. The flow diagram of FIG. 10 is an example of the techniques described by FIGS. 7-9. Although processing circuitry 210 is described as performing the technique of FIG. 10, other circuitry of IMD and/or other devices may perform some or all of the technique in other examples.

Processing circuitry 210 may receive an indication from sensing circuitry 206 whether the value of a characteristic of sensed one or more sensed ECAPs 536 from FIG. 5 may be outside of a target range (1000). When sensed ECAP values are within the target range (NO branch of 1000) processing circuitry 210 may hold the value of the set of parameter values, e.g. Ic and Ii, for the plurality of pulses (1002). Processing circuitry 210 may continue to monitor ECAP values. In this disclosure, "sensing an ECAP" and "measuring an ECAP" is equivalent to sensing one or more ECAP values, and "a value of a characteristic of the ECAP," such as, sensing a voltage amplitude as described above in relation to FIG. 4, by sensing circuitry 206.

If processing circuitry 210 determines that ECAP values are outside the target range (YES branch of 1000), processing circuitry 210 may check whether the ECAP values are higher than the ECAP high threshold (YES branch of 1004).

Processing circuitry 210 may decrement Ic and Ii (1010) until the one or more values of the set of values reaches a minimum value. In the example of FIG. 10, processing circuitry 210 may determine that the amplitude of current for the control pulses (Ic) has not reached the minimum value (NO branch of 1012) and continue to monitor ECAP values.

If the ECAP values are outside of the range, but not higher than the ECAP high threshold (NO branch of 1004), processing circuitry 210 may increment Ic and Ii (1008) and continue to monitor ECAP values. In other words, if the ECAP values are outside of the range, but less than the ECAP high threshold, the ECAP values must be less than the low ECAP threshold.

When processing circuitry 210 determines that Ic=0, i.e. the minimum value of control pulse amplitude (YES branch of 1012), processing circuitry may start a noise detection timer, Tdetect. If the ECAP values stay above ETH during Tdetect and Tdetect expires (YES branch of 1014), processing circuitry 210 may suspend ERS (1016) and begin to increment both Ic and Ii (1018) until Ic and Ii reach the default values, e.g. Ict 606 and Iit 608 from FIG. 6 (NO branch of 1020). When Ic and Ii reach the default values (YES branch of 1020), processing circuitry may hold Ic and Ii at the default values (1022) and monitor ECAP values. In other examples, (not shown in FIG. 10), processing circuitry 210 may set Ic and Ii directly to the default values during this period without the incremental increases.

As described above in relation to FIG. 8, in other examples, processing circuitry may increment both Ic and Ii (1018) until Ic and Ii reach a sub-default value (not shown in FIG. 10). In other words, processing circuitry may temporarily disable closed-loop operation in the presence of noise and return to some level of therapeutic energy. In some examples, the sub-default value may be a percentage of the default value (not shown in FIG. 10). In other examples, processing circuitry may return the parameter values to an average, median or some other calculated stimulation level collected during some interval prior to the detection of noise. For example, processing circuitry may use a moving window of delivered stimulation levels and calculate a parameter value over the duration of the moving window. If noise is detected, then the processing circuitry may return the parameter value to the calculated level determined prior to the initial noise detect.

As described above in relation to FIG. 9, when the ECAP values are less than ETH (YES branch of 1024) processing circuitry may start a low noise timer, e.g. Tlow-noise 920. When the low noise timer has expired (YES branch of 1026), processing circuitry 210 may restart the closed loop algorithm, e.g. ERS, (1028) and continue to monitor ECAP values.

Figure 11:
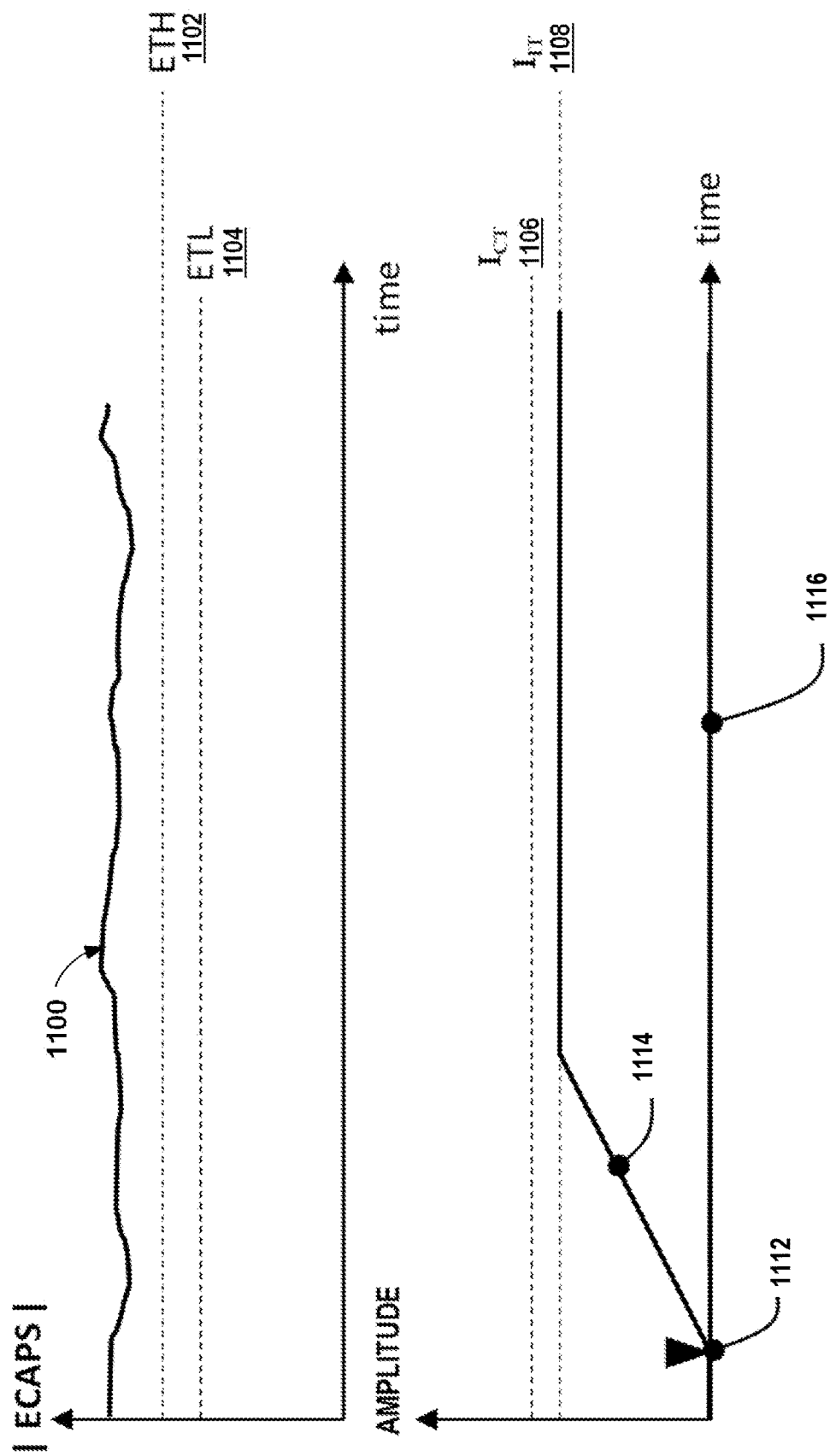
FIG. 11 is a timing diagram illustrating an example of a medical device providing electrical stimulation while suspending a closed loop algorithm, in accordance with one or more techniques of this disclosure.

FIG. 11 is a timing diagram illustrating an example of a medical device providing electrical stimulation while suspending a closed loop algorithm, in accordance with one or more techniques of this disclosure. The example of FIG. 11 provides an alternative option to the techniques described by FIGS. 7-10. In contrast to FIGS. 7 and 10, once processing circuitry 210 determines that ERS should be suspended (1112), e.g. because ECAPs value 1100 is above ETL 1104 and ETH 1102 for an extend time, processing circuitry 210 may increment only the informed pulse current amplitude Ii 1114 to the default value Iit 1108. The control pulse amplitude Ic, may remain at the minimum value, rather than returning to the default value of Ict 1106 (1116). Since the control pulse amplitude Ic is what elicits the sensed ECAP signal, a control pulse amplitude Ic at zero should not result in any detectable ECAP signal. In contrast, informed pulse current amplitude Ii can return to default value Iit 1108 in order to reestablish stimulation therapy.

Figure 12:
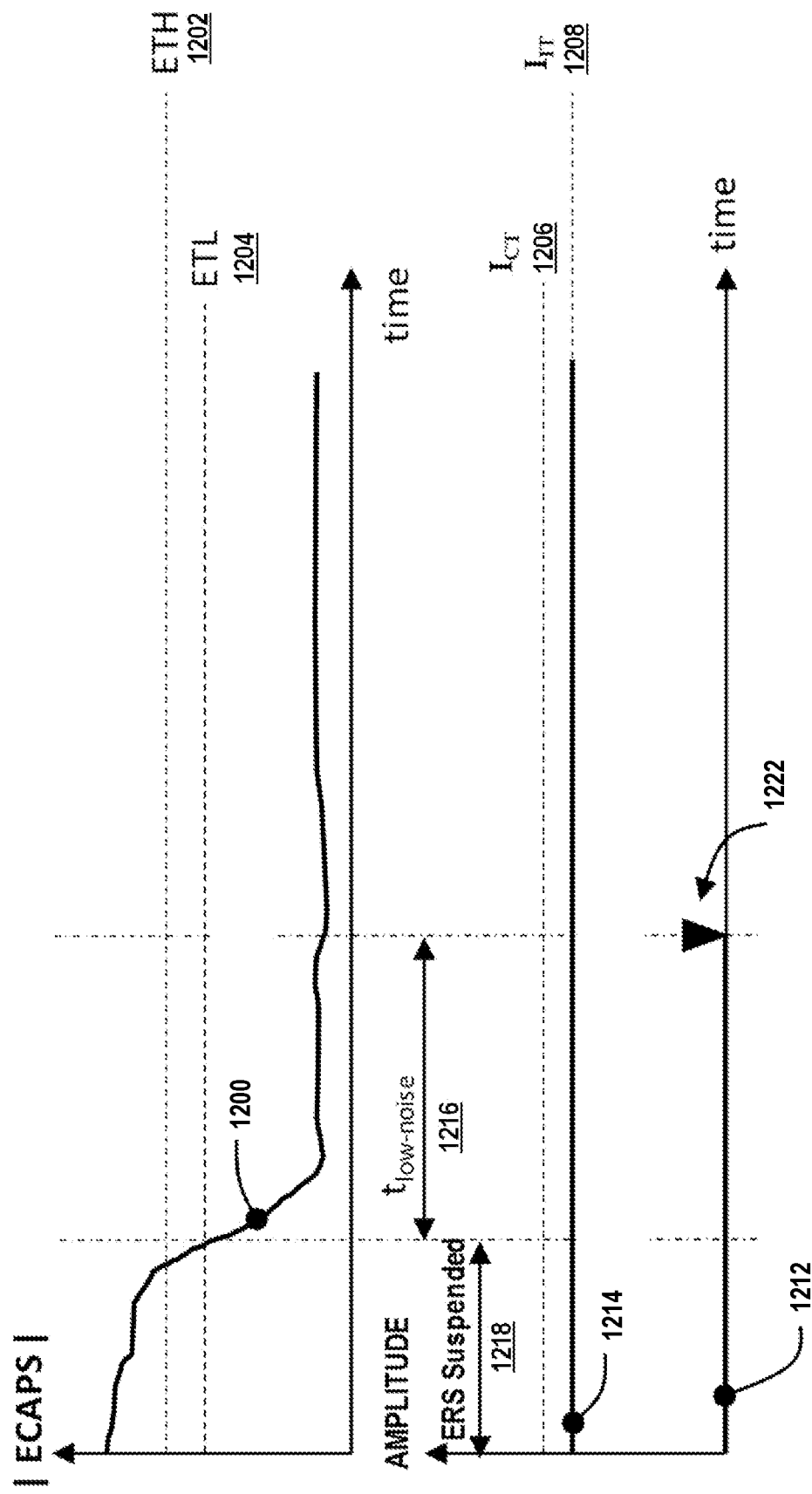
FIG. 12 is a timing diagram illustrating an example of a medical device sensing noise abatement while suspending a closed loop algorithm, in accordance with one or more techniques of this disclosure.

FIG. 12 is a timing diagram illustrating an example of a medical device sensing noise abatement while suspending a closed loop algorithm, in accordance with one or more techniques of this disclosure. As described above in relation to FIG. 11, processing circuitry 210 may increase informed pulse current amplitude Ii 1214 to the default value Iit 1208 while control pulse amplitude Ic 1212, may remain at the minimum value during noise detection and ERS is suspended 1218.

When the noise no longer affects the ECAP value, the ECAP value may drop below ETL 1204 because while the control pulse amplitude is zero (Ic=0), IMD 200 should not generate a detectable ECAP value (e.g., there should be no ECAP signal without a stimulation pulse to elicit such an ECAP signal). Processing circuitry 210 may receive an indication from sensing circuitry 206 that the ECAP value has settled below ETL 1204 (1200) and may start a low-noise timer $T_{low-noise}$ 1216. In the example of FIG. 12, processing circuitry may determine noise has abated when Ic=0, the ECAP value is below both ETH 1202 and ETL 1204 and $T_{low-noise}$ 1216 has expired (1222). Put another way, processing circuitry 210 may determine that the noise has abated because the ECAP value has dropped to expected levels with a lack of any control pulse being delivered that is capable of eliciting a detectable ECAP signal.

Figure 13:
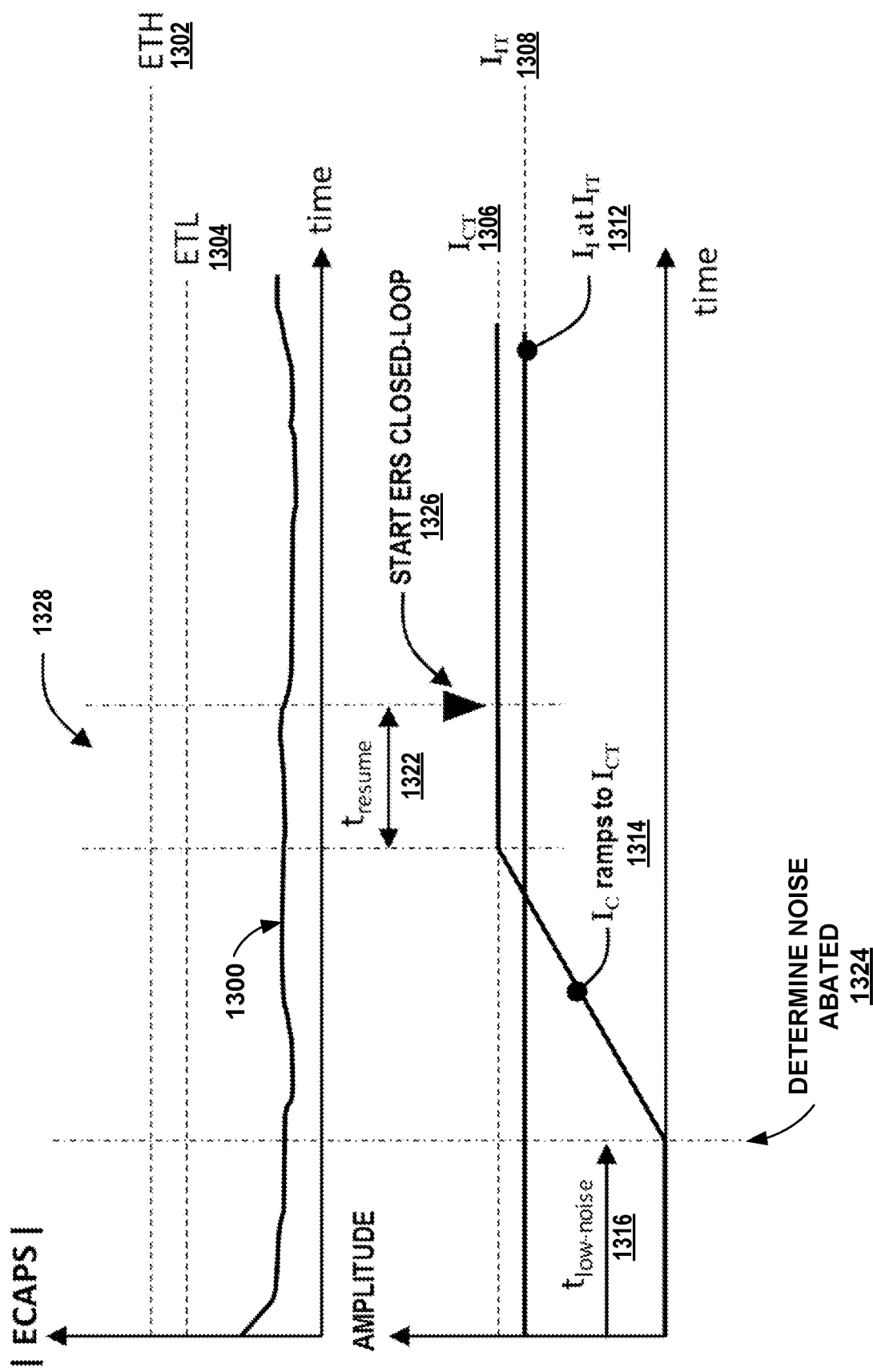
FIG. 13 is a timing diagram illustrating an example of re-starting a suspended closed-loop algorithm, in accordance with one or more techniques of this disclosure.

FIG. 13 is a timing diagram illustrating another example of recovering a suspended closed-loop algorithm, in accordance with one or more techniques of this disclosure. As described above in relation to FIG. 12, processing circuitry 210 may determine that noise impacting a sensed ECAPs value has abated when $T_{low-noise}$ 1316 has expired (1324).

Processing circuitry 210 may increase Ic 1314 until Ic 1314 reaches the default value of Ict 1306. The informed pulse current magnitude Ii 1312 may remain at Iit 1308. To ensure the noise is gone, processing circuitry 210 may start a confirmation timer, e.g. Tresume 1322, and only restart the closed loop algorithm when Tresume 1322 expires (1326). In other words, in response to determining that Ic 1314 is at Ict 1306, the ECAP value is less than ETL 1304 and the confirmation timer Tresume 1322 has expired, processing circuitry 210 may restart ERS (1328). In other examples, (not shown in FIG. 13) processing circuitry 210 may re-enable the closed loop algorithm rather than increasing the parameter values for Ic 1314 and Ii 1312 until the values reach the default value. In other words, processing circuitry 210 may re-enable the closed-loop algorithm such that IMD 200 may provide appropriate stimulation once the system determines that the noise source is gone.

Figure 14:
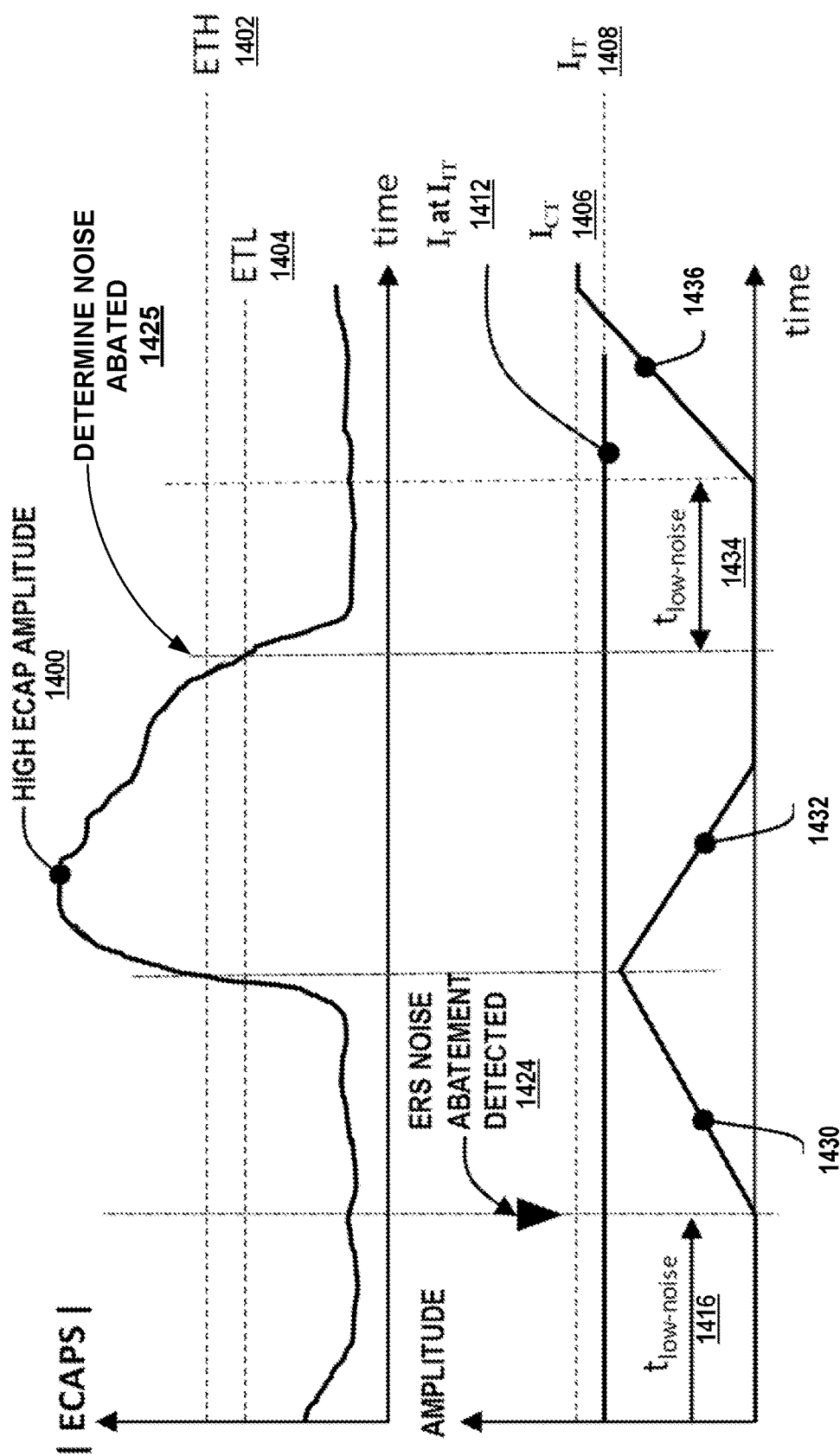
FIG. 14 is a timing diagram illustrating an example of an attempted recovery for a suspended closed-loop algorithm, in accordance with one or more techniques of this disclosure.

FIG. 14 is a timing diagram illustrating an example of an attempted recovery for a suspended closed-loop algorithm, in accordance with one or more techniques of this disclosure. As described above in relation to FIG. 13, when processing circuitry 210 determines that the noise has abated (1424), at the expiration of $T_{low-noise}$ 1416, processing circuitry 210 may increase Ic to the default value and start a confirmation timer, e.g. Tresume 1322. At some time in the interval between determining the noise has abated and the confirmation timer has expired, processing circuitry 210 may receive an indication from sensing circuitry 206 that the ECAP value has exceeded ETH 1402 (1400).

In the example of FIG. 14, Ic ramps toward Ict (1430) after processing circuitry determines noise has abated (1424). However, noise again couples to the sensing circuitry 206 of IMD 200 and processing circuitry 210 controls Ic to decrease toward the minimum value of Ic=0 (1432). In this manner, processing circuitry 210 can react to any restart of noise when attempting to reestablish ERS. When processing circuitry 210 again determines that the noise has abated (1425) because the ECAP value 1400 is less than ETH 1402 and ETL 1404, processing circuitry may again start a low noise timer, $T_{low-noise}$ 1434. When $T_{low-noise}$ 1434, processing circuitry 210 may re-attempt to ramp Ic toward Ict (1436). To avoid under stimulation, the informed pulse amplitude Ii 1412 may remain at the default value Iit 1408. Once processing circuitry 210 ramps Ic back to Ict, processing circuitry 210 can continue ERS as normal.

Figure 15:
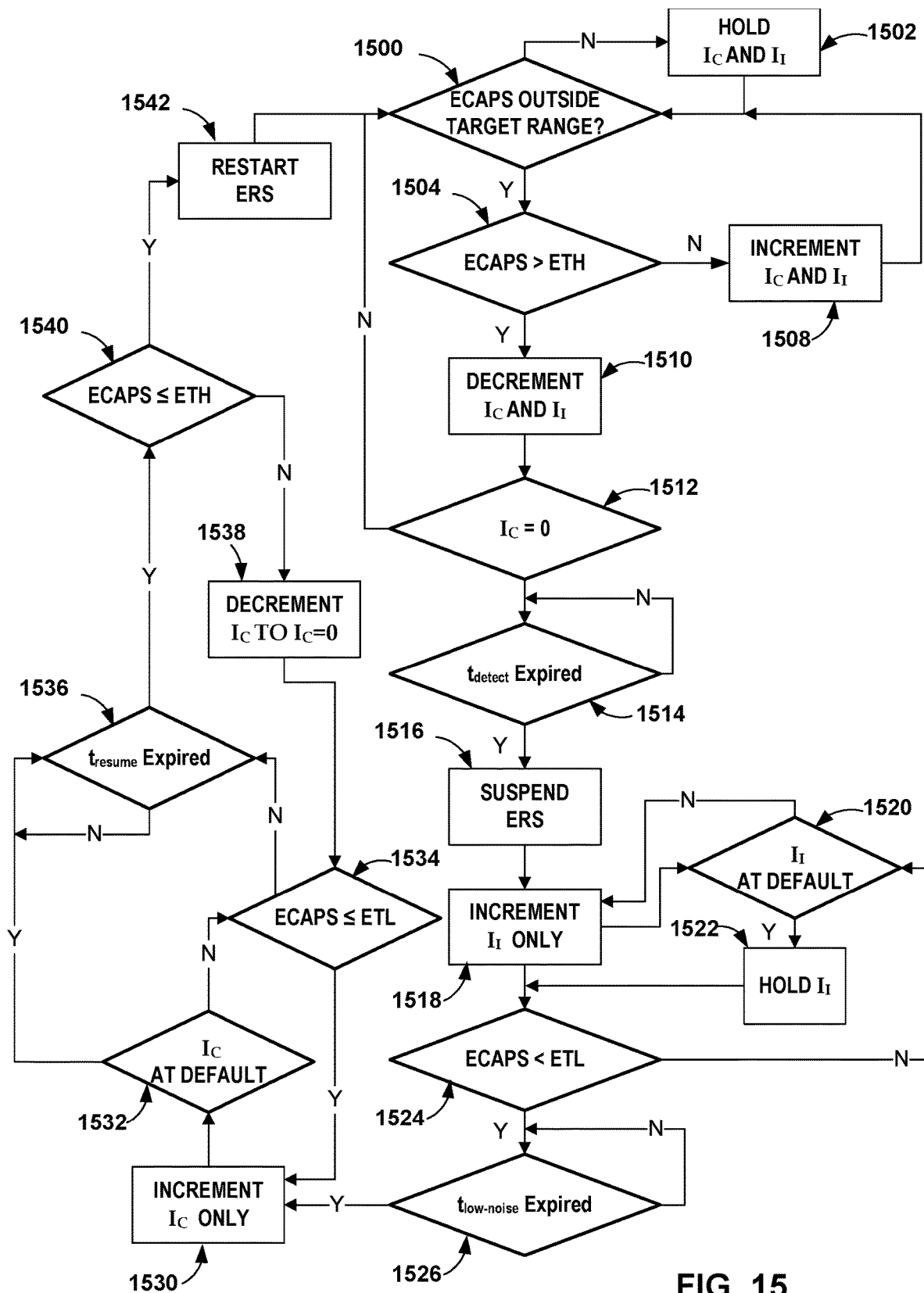
FIG. 15 is a flow diagram illustrating an example operation for suspending and recovering a suspended closed-loop algorithm, in accordance with one or more techniques of this disclosure.

FIG. 15 is a flow diagram illustrating another example operation for suspending and recovering a suspended closed-loop algorithm, in accordance with one or more techniques of this disclosure. The example of FIG. 15 describes techniques illustrated by FIGS. 11-14. Although processing circuitry 210 is described as performing the technique of FIG. 15, other circuitry of IMD and/or other devices may perform some or all of the technique in other examples.

Similar to FIG. 10 described above, processing circuitry 210 may receive an indication from sensing circuitry 206 whether the value of a characteristic of sensed one or more sensed ECAPs 536 from FIG. 5 may be outside of a target range (1500). When sensed ECAP values are within the target range (NO branch of 1500) processing circuitry 210 may hold the value of the set of parameter values, e.g. Ic and Ii, for the plurality of pulses (1502). Processing circuitry 210 may continue to monitor ECAP values.

If the ECAP values are outside of the range, but not higher than the ECAP high threshold (NO branch of 1504), processing circuitry 210 may increment Ic and Ii (1508) and continue to monitor ECAP values. In other words, if the ECAP values are outside of the range, but less than the ECAP high threshold, the ECAP values must be less than the low ECAP threshold.

When processing circuitry 210 determines that Ic=0, i.e. the minimum value of control pulse amplitude (YES branch of 1512), processing circuitry may start a noise detection timer, Tdetect. If the ECAP values stay above ETH during Tdetect and Tdetect expires (YES branch of 1514), processing circuitry 210 may suspend ERS (1516) and begin to increment only Ii (1518) until Ii reach the default value, e.g. Iit 608 from FIG. 6 (NO branch of 1520). When Ii reaches the default value (YES branch of 1520), processing circuitry may hold Ii at the default values (1522) and monitor ECAP values (NO branch of 1524). In this manner, IMD 200 may deliver therapy to patient 105 of FIG. 1 and avoid under stimulation caused by noise.

As described above in relation to FIGS. 12-14, when processing circuitry 210 receives an indication that the ECAP values are less than ETL, processing circuitry 210 may start $T_{low-noise}$. When expires, processing circuitry may begin to increase Ic only (1530) because Ii is already at the default value, Iit. As Ic is increasing, processing circuitry 210 may continue to monitor the ECAP values (NO branch of 1532). While the ECAP values remain less than or equal to ETL (YES branch of 1534), processing circuitry 210 may continue to increase Ic (1530).

When Ic reaches the default value, Ict (YES branch of 1532), processing circuitry 210 may start a confirmation timer Tresume, described above in relation to FIGS. 13 and 14. If the ECAP values exceed the ECAP high threshold (NO branch of 1540) after the confirmation timer expires (YES branch of 1536), processing circuitry 210 may decrement Ic (1538) back to the minimum value of IC, and continue to monitor the ECAP values. If the ECAP values remain less than ETH (YES branch of 1540), then processing circuitry 210 may restart the closed loop algorithm, e.g. ERS (1542).

Figure 16:
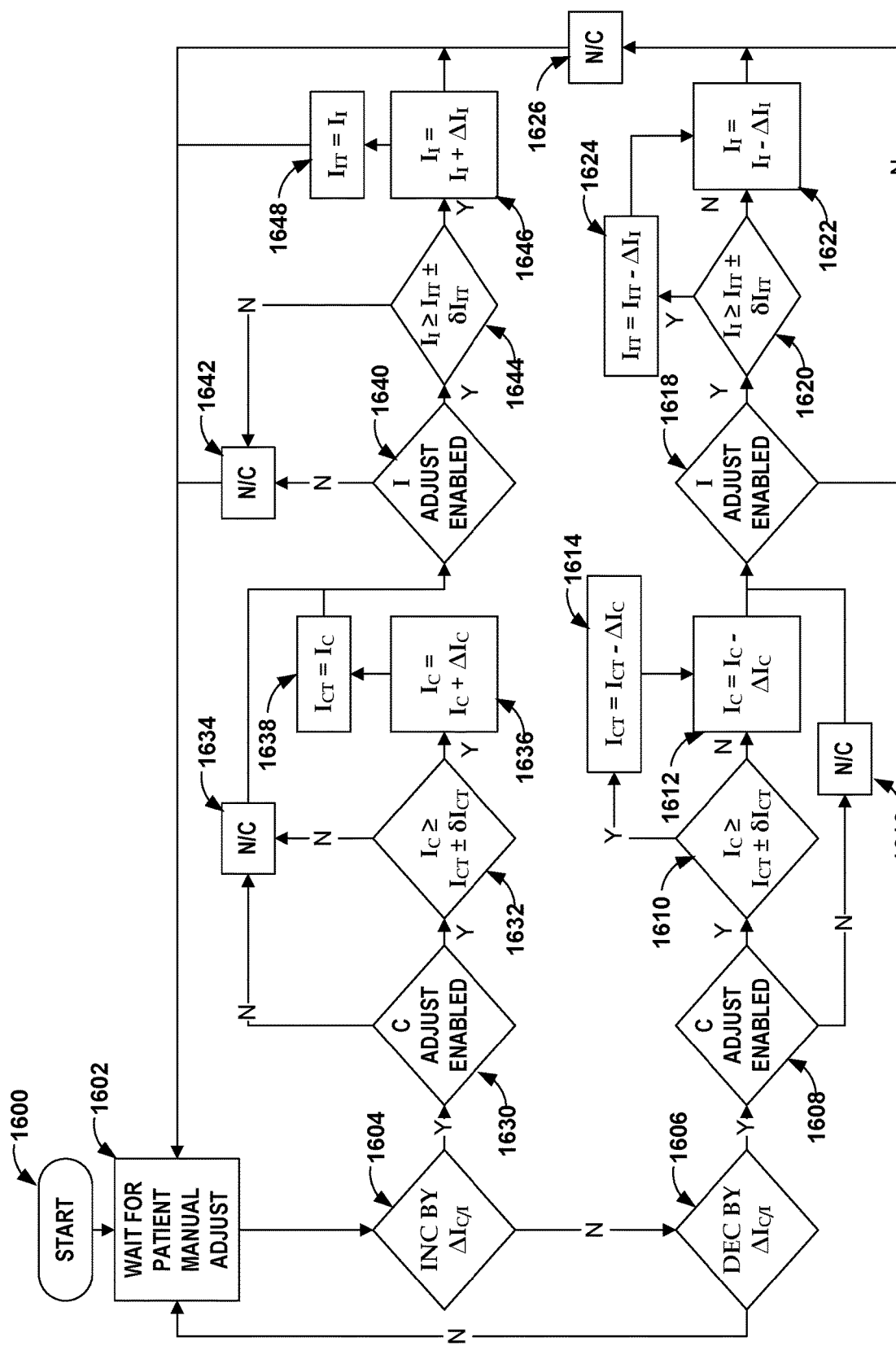
FIG. 16 is a flow chart illustrating an example operation for managing patient input while delivering electrical stimulation therapy, in accordance with one or more techniques of this disclosure.

FIG. 16 is a flow chart illustrating an example operation for managing patient input while delivering electrical stimulation therapy, in accordance with one or more techniques of this disclosure. As described above in relation to FIGS. 5 and 7, it may be desirable to disable certain programming commands from external programmer 150 while an IMD of this disclosure is responding to patient physiological signals or to noise.

In example of FIG. 16, the system may only increment therapy (e.g. increase amplitude) in response to a patient adjustment if the current control pulse and informed amplitude levels, Ic and Ii, are approximately equal to the default levels, Ict and Iit, respectively. As described above in relation to FIGS. 5-15, one or both of Ic and Ii, may approximately equal the default levels, Ict and Iit, when ERS is disabled for a particular. One or both of Ic and Ii may approximately equal the default levels ERS was enabled, but not actively suppressing stimulation therapy levels due to high ECAP measurements. If Ic and/or Ii are not at their default levels (e.g. being suppressed by the ERS algorithm), then the system, may not increase the therapy and, more importantly, may not increase the default levels, according to the techniques of this disclosure. As described above in relation to FIG. 2, the "system" and "processing circuitry 210" may refer to IMD 110 and IMD 200 alone, or in communication with external programmer 150.

In some examples, the patient may choose to decrement the therapy amplitude. Should the patient decrease therapy amplitude then the system may decrement the amplitude of the stimulation therapy being delivered. In addition, if the stimulation pulse amplitude (Ic or Ii) are at the default levels of Ict and Iit, respectively, then the request to decrement the therapy may also adjust the default amplitude level, Ict and Iit.

The techniques of this disclosure will therefore permit the system to be responsive to patient requests, especially to decrement a therapy, but may avoid unwanted conditions where a patient may increase a default stimulation level without a real-time increase in the therapy being delivered and perceived by the patient. In this manner, the techniques of this disclosure may prevent issues of incorrect default level adjustments above a comfortable level when a closed-loop therapy algorithm has altered the stimulation levels away from the normal default stimulation levels for either a control pulse waveform or an informed pulse waveform in the presence of noise or other sensing issue. Thus, a closed-loop responsive stimulation system of this disclosure that includes the ability of patient adjustment needs may account for situations when the system is responding to changes in physiological signals or noise.

At the start (1600) of FIG. 16, processing circuitry 210 may continue to monitor ECAP values and deliver electrical stimulation therapy as needed while waiting for manual adjustment commands from a patient programmer (1602). In some examples, processing circuitry 210 may receive a command to increment one or both of the control pulse parameter, e.g. Ic, or the informed pulse parameter, e.g. Ii by a specified amount. In the example of FIG. 16, the specified increment (YES branch of 1604) is $\Delta I_{C/I}$, which indicates an increase in either or both of $\Delta Ic$ or $\Delta Ii$.

Note that in the example of FIG. 16, an increase in $\Delta Ic$ or $\Delta Ii$ corresponds to an increase in stimulation level. Similarly, an increase in other parameters for the control pulse or the informed pulse may also increase the stimulation level. Some examples may include an increase in voltage magnitude, an increase in duty cycle, an increase in pulse width and similar parameters may increase the stimulation level. In other examples, requested changes to parameters may decrease the stimulation level. For example, selecting different electrodes, changing the output impedance and other parameter changes may decrease stimulation levels. The increase of block 1604 and decrease of block 1606 use changes in electrical current amplitude as in an example of an increase or decrease in stimulation level and the description of FIG. 16 should not be interpreted limited to just an increase or decrease in current amplitude, but interpreted more broadly as an increase or decrease in stimulation level.

In some examples, processing circuitry 210 may include a setting, e.g. stored at storage device 212, that disables any manual adjustments in the control pulse parameters (NO branch of 1630). If changes to Ic are disabled, then a command to increase Ic would result in no change (1634). In the example of FIG. 16, at any time that processing circuitry 210 rejects a request from the patient programmer, processing circuitry 210 may communicate with the patient programmer, e.g., external device 30, and provide an indication that the request has been rejected. For example, at the NO branch of 1630, 1632, 1644, 1608 and so on.

Processing circuitry 210 may be further configured to disable any manual adjustments in the informed pulse parameters (NO branch of 1640). If changes to Ii are disabled, then a command to increase Ii would result in no change (1642) and processing circuitry may continue to monitor for manual adjustments (1602).

In other examples, processing circuitry 210 may enable adjustments to Ic (YES branch of 1630) and processing circuitry 210 may determine whether the set of parameter values for the electrical stimulation therapy is approximately equal to a default set of parameter values, e.g., whether $I_C \geq I_{CT} \pm \delta I_{CT}$. When Ic is outside the predetermined range of the respective default parameter value, e.g. differs from Ict by more than $\pm \delta I_{CT}$, (NO branch of 1632), then processing circuitry 210 may not increment Ic (1634). When Ic is with the predetermined range (YES branch of 1632), processing circuitry 210 may increment Ic by $\Delta$Ic (1636) and change the default value Ict to the new value of Ic (1638). Said another way, processing circuitry 210, may first determine that the value of the parameter defining the electrical stimulation therapy is not within a tolerance, $\pm \delta I_{CT}$, of a default parameter before rejecting the request to change the parameter. The tolerance, $\pm \delta I_{CT}$, is a small value, compared to the default value, that may be zero.

In examples in which processing circuitry 210 may enable adjustments to Ii (YES branch of 1640) and processing circuitry 210 may determine whether the set of parameter values for the electrical stimulation therapy is approximately equal to a default set of parameter values, e.g., whether $I_i \geq I_{IT} \pm \delta I_{IT}$. When Ii is outside the predetermined range of the respective default parameter value, e.g. differs from Iit by more than $\pm \delta I_{IT}$, (NO branch of 1644), then processing circuitry 210 may not increment Ii (1642). When Ii is with the predetermined range (YES branch of 1644), processing circuitry 210 may increment Ii by $\Delta$Ii (1646) and change the default value Iit to the new value of Ii (1688).

In other examples, processing circuitry may receive a decrement command from external programmer 150 (NO branch of 1604 and YES branch of 1606).

Processing circuitry 210 may be configured to disable any manual adjustments in the control pulse parameters (NO branch of 1608). If changes to Ic are disabled, then a command to decrease Ic would result in no change (1616).

Processing circuitry 210 may be further configured to disable any manual adjustments in the informed pulse parameters (NO branch of 1618). If changes to Ii are disabled, then a command to decrease Ii would result in no change (1626) and processing circuitry may continue to monitor for manual adjustments (1602).

In other examples, processing circuitry 210 may be configured to enable adjustments to Ic (YES branch of 1608) and processing circuitry 210 may determine whether the set of parameter values for the electrical stimulation therapy is approximately equal to a default set of parameter values, e.g., whether $I_C \geq I_{CT} \pm \delta I_{CT}$. When Ic is outside the predetermined range of the respective default parameter value, e.g. differs from Ict by more than $\pm \delta I_{CT}$, (NO branch of 1610), then, in contrast to the increment command, processing circuitry 210 may decrement Ic by $\Delta$Ic, i.e. Ic=Ic–$\Delta$Ic (1612), but make no change to the default value Ict. In other examples, when Ic is with the predetermined range (YES branch of 1610), processing circuitry 210 may decrement both Ic by $\Delta$Ic (1612) and change the default value Ict to the new value of Ic, i.e. Ict=Ict–$\Delta$Ic (1614).

In examples in which processing circuitry 210 may enable adjustments to Ii (YES branch of 1618) and processing circuitry 210 may determine whether the set of parameter values for the electrical stimulation therapy is approximately equal to a default set of parameter values, e.g., whether $I_i \geq I_{IT} \pm \delta I_{IT}$. When Ii is outside the predetermined range of the respective default parameter value, e.g. differs from Et by more than $\pm$(NO branch of 1620), in contrast to the increment command, processing circuitry 210 may decrement Ii by $\Delta$Ii, i.e. Ii=Ii–$\Delta$Ii (1622), but make no change to the default value Iit. In other examples, when Ii is with the predetermined range (YES branch of 1620), processing circuitry 210 may decrement both Ii by $\Delta$Ii (1622) and change the default value Iit to the new value of Ii, i.e. Iit=Iit–$\Delta$Ii (1624).

In one or more examples, the functions described above may be implemented in hardware, software, firmware, or any combination thereof. For example, the various components of FIGS. 1 and 2, such as processing circuitry 210, sensing circuitry 206, and communication circuitry 208 may be implemented in hardware, software, firmware, or any combination thereof. If implemented in software, the functions may be stored on or transmitted over, as one or more instructions or code, a computer-readable medium and executed by a hardware-based processing unit. Computer-readable media, such as storage device 212, may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium. The term "non-transitory" may indicate that the storage medium is not embodied in a carrier wave or a propagated signal. In certain examples, a non-transitory storage medium may store data that can, over time, change (e.g., in RAM or cache).

By way of example, and not limitation, such computer-readable storage media, such as storage device 212, may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Combinations of the above should also be included within the scope of computer-readable media.

Instructions may be executed by one or more processors, such as one or more DSPs, general purpose microprocessors, ASICs, FPGAs, or other equivalent integrated or discrete logic circuitry. Accordingly, the term "processor," as used herein, such as processing circuitry 210, may refer to any of the foregoing structure or any other structure suitable for implementation of the techniques described herein. Also, the techniques could be fully implemented in one or more circuits or logic elements.

The techniques of this disclosure may be implemented in a wide variety of devices or apparatuses, including, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Example 1: A method that includes receiving information indicative of a sensed evoked compound action potential (ECAP) signal; determining a value of a characteristic of the ECAP signal based on the information, wherein the ECAP signal is elicited by a respective stimulation pulse of a plurality of stimulation pulses; executing a closed loop policy that adjusts, based on the value of the characteristic of the ECAP signal, a value of a parameter that at least partially defines stimulation therapy; determining that the value of the characteristic of the ECAP signal is outside of an expected range; and responsive to determining that the value of the characteristic of the ECAP signal is outside of the expected range, disabling the closed loop policy.

Example 2: The method of example 1, wherein the value of the parameter is a first value, wherein a set of values for the parameter comprises a threshold value, and wherein the method further comprises: responsive to adjusting the first value to the threshold value based on the closed loop policy, starting a noise detection timer; determining that the noise detection timer has expired; and responsive to determining that the noise detection timer has expired, determining that the value of the characteristic of the ECAP signal remains outside of the expected range; and responsive to determining that the value of the characteristic of the ECAP signal remains outside of the expected range, disabling the closed-loop policy.

Example 3: The method of example 2, wherein the threshold value of the parameter of the respective stimulation pulses comprises a minimum value for the parameter.

Example 4: The method of example 2, wherein the plurality of pulses comprises a plurality of control pulses and a plurality of informed pulses, wherein the respective stimulation pulses comprise respective control pulses of the plurality of control pulses, wherein receiving information indicative of a ECAP signal comprises sensing a respective ECAP signal after a respective control pulse of the plurality of control pulses, wherein an informed pulse of the plurality of informed pulses is defined by one or more parameters based on a respective ECAP signal elicited from a respective control pulse while executing the closed loop policy; wherein the expected range of the value of the characteristic comprises an ECAP high threshold (ETH) and an ECAP low threshold (ETL), and wherein the method further comprises: responsive to the value of the characteristic of the ECAP signal greater than the ECAP high threshold, incrementally adjusting: a respective value of the parameter defining the plurality of respective control pulses from a first control pulse value toward a second control pulse value; and a respective value of the parameter defining the plurality of respective informed pulses from a first informed pulse value toward a second informed pulse value.

Example 5: The method of example 4, further that includes responsive to disabling the closed loop policy, adjusting, by the processing circuitry, informed pulse parameter values back to the first informed pulse value, and measuring, by the sensing circuitry, the respective ECAP signal after the respective control pulse, wherein the processing circuitry makes no adjustments to informed pulse parameter values nor control pulse parameter values based on the measured respective ECAP signal while the closed loop policy is disabled.

Example 6: The method of example 4, further comprising, responsive to sensing, by the sensing circuitry, that the value of the characteristic of the measured respective ECAP signal is less than the ECAP high threshold, starting, by the processing circuitry a low-noise timer.

Example 7: The method of example 6, further comprising, responsive to determining, by the processing circuitry, that the low-noise timer has expired, enabling, by the processing circuitry, the closed-loop policy.

Example 8: The method of example 5, wherein the first informed pulse value of the parameter is a control pulse parameter default value, wherein the second control pulse value is less than or equal to the default value, and wherein the control pulse parameter is set to the second control pulse value, the method further comprising, in response to in response to receiving an indication from the sensing circuitry that the value of the characteristic of the measured respective ECAP signal is less than the ECAP low threshold, start a low-noise timer; responsive to determining that the low-noise timer has expired, adjusting, by the processing circuitry, the control pulse parameter values from the second control pulse value to the default value.

Example 9: The method of example 8, further that includes responsive to setting the control pulse parameter values to the default value, starting, by the processing circuitry, a confirmation timer, and responsive to determining that the confirmation timer has expired, enabling, by the processing circuitry, the closed-loop policy.

Example 10: The method of example 8, further that includes responsive to sensing, by the sensing circuitry, that the value of the characteristic of the measured respective ECAP signal is greater than the ECAP high threshold, reducing, by the processing circuitry, the respective value of the parameter for the plurality of respective control pulses; and the respective value of the parameter for the plurality of respective informed pulses.

Example 11: The method of example 10, further that includes responsive to determining that the low-noise timer has expired, adjusting, by the processing circuitry, control pulse value from the second control value to the default control pulse value, responsive to setting the control pulse parameter values to the default control pulse value, starting, by the processing circuitry, a confirmation timer, and responsive to determining that the confirmation timer has expired, enabling, by the processing circuitry, the closed-loop policy.

Example 12: The method of example 1, further comprising controlling the stimulation generation circuitry to deliver electrical stimulation therapy according to: the closed loop policy, or user input.

Example 13: A medical device comprising processing circuitry configured to: receive information indicative of a sensed evoked compound action potential (ECAP) signal determine a value of a characteristic of the ECAP signal based on the information, wherein the ECAP signal is elicited by respective stimulation pulses of a plurality of pulses; determine whether a value of a characteristic of the ECAP signal is outside of an expected range; execute a closed loop policy, wherein the closed loop policy adjusts a value of a parameter that at least partially defines stimulation therapy, based on the value of the characteristic of the ECAP signal; and responsive to determining that the value of the characteristic of the ECAP signal is outside of the expected range, disable the closed-loop policy.

Example 14: The medical device of example 13, wherein the value of the parameter is a first value, wherein a set of values for the parameter comprises a threshold value; the processing circuitry further configured to: responsive to adjusting the value of the parameter from the first value to the threshold value, starting, a noise detection timer; responsive to determining that the noise detection timer has expired, and that the value of the characteristic of the ECAP signal is still outside of the expected range, disable the closed-loop policy.

Example 15: The medical device of example 14, wherein the threshold value of the parameter of the respective stimulation pulses comprises a minimum value for the parameter.

Example 16: The medical device of example 15: wherein the plurality of pulses comprises a plurality of control pulses and a plurality of informed pulses, wherein the respective stimulation pulses comprise respective control pulses of the plurality of control pulses, wherein receiving information indicative of a ECAP signal comprises sensing a respective ECAP signal after a respective control pulse of the plurality of control pulses, wherein an informed pulse of the plurality of informed pulses is defined by one or more parameters based on a respective ECAP signal elicited from a respective control pulse, wherein the expected range of the value of the characteristic comprises an ECAP high threshold (ETH) and an ECAP low threshold (ETL), the processing circuitry further configured to, responsive to the value of the characteristic of the ECAP signal greater than the ECAP high threshold, incrementally adjusting: a respective value of the parameter for the plurality of respective control pulses from a first control pulse value toward a second control pulse value; and a respective value of the parameter for the plurality of respective informed pulses from a first informed pulse value toward a second informed pulse value.

Example 17: The medical device of example 16, wherein the processing circuitry is further configured to: responsive to disabling the closed loop policy, adjust the informed pulse parameter values back to the first informed pulse values, and cause the sensing circuitry to measure the respective ECAP signal after the respective control pulse, wherein the processing circuitry makes no adjustments to the informed pulse parameter values nor the control pulse parameter values based on the measured respective ECAP signal while the closed loop policy is disabled.

Example 18: The medical device of example 17, wherein the processing circuitry further configured to, responsive to receiving an indication from the sensing circuitry that the value of the characteristic of the measured respective ECAP signal is less than the ECAP high threshold, start a low-noise timer.

Example 19: The medical device of example 18, wherein the processing circuitry is further configured to, responsive to determining that the low-noise timer has expired, enable the closed-loop policy.

Example 20: The medical device of example 16, wherein the first informed pulse value of the parameter is a control pulse parameter default value, wherein the second control pulse value is less than or equal to the default value, and wherein the control pulse parameter is set to the second control pulse value, wherein the processing circuitry further configured to: responsive to receiving an indication from the sensing circuitry that the value of the characteristic of the measured respective ECAP signal is less than the ECAP low threshold, start a low-noise timer; and responsive to determining that the low-noise timer has expired, adjust the control pulse parameter values from the second control pulse value to the default control pulse value.

Example 21: The medical device of example 20, wherein the processing circuitry is further configured to, responsive to setting the control pulse parameter values to the default control pulse value, start a confirmation timer, and responsive to determining that the confirmation timer has expired, enable the closed-loop policy.

Example 22: The medical device of example 20, wherein the processing circuitry is further configured to, responsive to receiving an indication from the sensing circuitry, that the value of the characteristic of the measured respective ECAP signal is greater than the ECAP high threshold, reducing the respective value of the parameter for the plurality of respective control pulses.

Example 23: The medical device of example 22, wherein the processing circuitry is further configured to, responsive to determining that the low-noise timer has expired, adjust the control pulse parameter values from the second control pulse value to the default control pulse value, responsive to setting the control pulse parameter values to the default control pulse value, start a confirmation timer, and responsive to determining that the confirmation timer has expired, enable the closed-loop policy.

Example 24: The medical device of example 13, wherein the processing circuitry is further configured to control the stimulation generation circuitry to deliver electrical stimulation therapy according to: the closed loop policy, or user input.

Example 25: A computer-readable medium comprising instructions for causing programmable processor processing circuitry to: receive information indicative of a sensed evoked compound action potential (ECAP) signal determine a value of a characteristic of the ECAP signal based on the information, wherein the ECAP signal is elicited by respective stimulation pulses of a plurality of pulses; determine whether a value of a characteristic of the ECAP signal is outside of an expected range; execute a closed loop policy, wherein the closed loop policy adjusts a value of a parameter that at least partially defines stimulation therapy, based on the value of the characteristic of the ECAP signal; and responsive to determining that the value of the characteristic of the ECAP signal is outside of the expected range, disable the closed-loop policy.

Example 26: A method that includes delivering, by stimulation generation circuitry of a medical device, electrical stimulation therapy to a patient, the electrical stimulation therapy comprising a plurality of pulses defined by a set of parameters; receiving, by processing circuitry of the medical device, a request from an external programmer to change a value of a parameter defining the plurality of pulses, wherein the external programmer is external to the medical device; determining, by the processing circuitry, that the requested change to the parameter is a request to increase the value of the parameter defining the plurality of pulses; determining, by the processing circuitry, that a control policy executed by the processing circuitry is determining values of the parameter that defines the electrical stimulation therapy; responsive to determining that the control policy is determining values of at the parameter that defines the electrical stimulation therapy, rejecting, by the processing circuitry, the request to change the value of the parameter.

Example 27: The method of example 26, wherein determining that the control policy is determining values of the parameter that defines the electrical stimulation therapy comprises: determining, by the processing circuitry, that the value of the parameter defining the electrical stimulation therapy is not within a tolerance of a default parameter; responsive to determining that the value of the parameter defining the electrical stimulation therapy is not within the tolerance of the default parameter, rejecting, by the processing circuitry the request to increase the value of the parameter.

Example 28: The method of any combination of examples 26-27, wherein the command from the external programmer is a is a first command, the method further that includes receiving, from the external programmer, a second command to change the value of the parameter defining the plurality of pulses; determining, by the processing circuitry, that the requested change to the parameter in the second command is also a request to increase the value of the parameter defining the plurality of pulses; responsive to determining that the value of the parameter defining the electrical stimulation therapy is within the tolerance of the default parameter, increasing, by the processing circuitry both the parameter and the default parameter based on the command from the external programmer.

Example 29: The method of any combination of examples 26-28, wherein the command from the external programmer is a is a first command, the method further that includes receiving, from the external programmer, a second command to change the value of the parameter defining the plurality of pulses; determining, by the processing circuitry, that the requested change to the parameter in the second command is a request to decrease the value of the parameter defining the plurality of pulses; responsive to determining that the requested change is a request to decrease the value of the parameter, changing, by the processing circuitry both the parameter and a default value of the parameter.

Example 30: The method of any combination of examples 26-29, further comprising, responsive to determining that the requested change is a request to decrease the value of the parameter, and before changing both the parameter and the default value of the parameter; determining that the value of the parameter defining the electrical stimulation therapy is within the tolerance of the default parameter; responsive to determining that the value of the parameter defining the electrical stimulation therapy is within a tolerance of the default parameter, changing, by the processing circuitry both the parameter and the default value of the parameter.

Example 31: The method of any combination of examples 26-30, wherein the parameter is an electrical current amplitude.

Example 32: The method of any combination of examples 26-31, wherein the set of parameters comprises the current amplitude that at least partially defines an informed pulse, and wherein the method further comprises: controlling the stimulation generation circuitry to deliver a control pulse configured to elicit a detectable evoked compound action potentials (ECAP) signal; receiving the ECAP signal; and executing the control policy to determine, based on the ECAP signal elicited by the delivered control pulse, an updated value of the current amplitude that at least partially defines a subsequent informed pulse and an updated value of a current amplitude that at least partially defines a subsequent control pulse.

Example 33: The method of any combination of examples 26-32, further comprising, outputting, by the processing circuitry of the medical device, an indication to the external programmer that the processing circuitry has rejected the request to change the value of the parameter.

Example 34: A medical device that includes stimulation generation circuitry configured to deliver electrical stimulation therapy to a patient, the electrical stimulation therapy comprising a plurality of pulses defined by a set of parameters; and processing circuitry configured to: receive a command from an external programmer (1602) to change a value of a parameter defining the plurality of pulses, wherein the external programmer is external to the medical device; determine that the requested change to the parameter is a request to increase the value of the parameter defining the plurality of pulses; determining that a control policy executed by the processing circuitry is determining values of the parameter that defines the electrical stimulation therapy responsive to determining that the control policy is determining values of at the parameter that defines the electrical stimulation therapy, reject the request to change the value of the parameter.

Example 35: The medical device of example 34, wherein to determine that the control policy is determining values of at the parameter that defines the electrical stimulation therapy comprises the processing circuitry configured to: determine that the value of the parameter defining the electrical stimulation therapy is with the tolerance of a default parameter; responsive to determining that the value of the parameter defining the electrical stimulation therapy is not within the tolerance of the default parameter, reject the request to change to the parameter to increase the value of the parameter.

Example 36: The medical device of any combination of examples 34-35, wherein the parameter value is an electrical current amplitude.

Example 37: The medical device of any combination of examples 34-36, wherein the command from the external programmer is a is a first command, and wherein the processing circuitry is further configured to: receive a second command to change the value of the parameter defining the plurality of pulses; determine that the requested change to the parameter in the second command is also a request to increase the value of the parameter defining the plurality of pulses; responsive to determining that the value of the parameter defining the electrical stimulation therapy is within the tolerance of the default parameter, increase both the parameter and the default parameter based on the command from the external programmer.

Example 38: The medical device of any combination of examples 34-37, wherein the command from the external programmer is a is a first command, and wherein the processing circuitry is further configured to: receive a second command from the external programmer to change the value of the parameter defining the plurality of pulses; determine that the requested change to the parameter in the second command is a request to decrease the value of the parameter defining the plurality of pulses; responsive to determining that the requested change is a request to decrease the value of the parameter, change both the parameter and a default value of the parameter.

Example 39: The medical device of any combination of examples 34-38, wherein the set of parameters comprises the current amplitude that at least partially defines an informed pulse, and wherein the method further comprises: controlling the stimulation generation circuitry to deliver a control pulse configured to elicit a detectable evoked compound action potentials (ECAP) signal; receiving the ECAP signal; and executing the control policy to determine, based on the ECAP signal elicited by the delivered control pulse, an updated value of the current amplitude that at least partially defines a subsequent informed pulse and an updated value of a current amplitude that at least partially defines a subsequent control pulse.

Example 40: The medical device of any combination of examples 34-39, wherein the processing circuitry of the medical device is configured to output an indication to the external programmer that the processing circuitry has rejected the request to change the value of the parameter.

Example 41: A computer-readable medium comprising instructions for causing a programmable processor of a medical device to: cause stimulation generation circuitry of the medical device to deliver electrical stimulation therapy to a patient, the electrical stimulation therapy comprising a plurality of pulses defined by a set of parameters; receive of the medical device, a command from an external programmer to change a value of a parameter defining the plurality of pulses, wherein the external programmer is external to the medical device; determine that the requested change to the parameter is a request to increase the value of the parameter defining the plurality of pulses; determine that a control policy executed by the processing circuitry is determining values of the parameter that defines the electrical stimulation therapy; responsive to determining that the control policy is determining values of at the parameter that defines the electrical stimulation therapy, reject the request to change the value of the parameter.

Example 42: The computer-readable medium of example 41, wherein determining that the control policy is determining values of the parameter that defines the electrical stimulation therapy comprises: determining, by the processing circuitry, that the value of the parameter defining the electrical stimulation therapy is not within a tolerance of a default parameter; responsive to determining that the value of the parameter defining the electrical stimulation therapy is not within the tolerance of the default parameter, rejecting, by the processing circuitry the request to increase the value of the parameter.

Example 43: The computer-readable medium of any combination of examples 41-42, wherein the command from the external programmer is a is a first command, the method further that includes receiving, from the external programmer, a second command to change the value of the parameter defining the plurality of pulses; determining, by the processing circuitry, that the requested change to the parameter in the second command is also a request to increase the value of the parameter defining the plurality of pulses; responsive to determining that the value of the parameter defining the electrical stimulation therapy is within the tolerance of the default parameter, increasing, by the processing circuitry both the parameter and the default parameter based on the command from the external programmer.

Example 44: The computer-readable medium of any combination of examples 41-43, wherein the command from the external programmer is a is a first command, the method further that includes receiving, from the external programmer, a second command to change the value of the parameter defining the plurality of pulses; determining, by the processing circuitry, that the requested change to the parameter in the second command is a request to decrease the value of the parameter defining the plurality of pulses; responsive to determining that the requested change is a request to decrease the value of the parameter, changing, by the processing circuitry both the parameter and the default value of the parameter.

Example 45: The computer-readable medium of any combination of examples 41-44, wherein the parameter is an electrical current amplitude.

Various examples of the disclosure have been described. These and other examples are within the scope of the following claims.

What is claimed is:

1. A method comprising:
    receiving information indicative of a sensed evoked compound action potential (ECAP) signal;
    determining a value of a characteristic of the ECAP signal based on the information, wherein the ECAP signal is elicited by a respective stimulation pulse of a plurality of stimulation pulses;
    executing a closed loop policy that adjusts, based on the value of the characteristic of the ECAP signal, a value of a parameter that at least partially defines stimulation therapy;
    determining whether the value of the characteristic of the ECAP signal is inside or outside of an expected range;
    responsive to determining that the value of the characteristic of the ECAP signal is outside of the expected range, disabling the closed loop policy and setting the parameter to a threshold value;
    responsive to setting the parameter to the threshold value, starting a noise detection timer; and
    responsive to determining that the noise detection timer has expired, enabling the closed loop policy.

2. The method of claim 1, further comprising
    responsive to determining that the noise detection timer has expired, determining that the value of the characteristic of the ECAP signal remains outside of the expected range; and
    responsive to determining that the value of the characteristic of the ECAP signal remains outside of the expected range, disabling the closed-loop policy.

3. The method of claim 2, wherein the threshold value of the parameter of the respective stimulation pulses comprises a minimum value for the parameter.

4. The method of claim 1,
wherein the plurality of stimulation pulses comprises a plurality of control pulses and a plurality of informed pulses,
wherein the respective stimulation pulses comprise respective control pulses of the plurality of control pulses,
wherein receiving information indicative of a ECAP signal comprises sensing a respective ECAP signal after a respective control pulse of the plurality of control pulses,
wherein an informed pulse of the plurality of informed pulses is defined by one or more parameters based on a respective ECAP signal elicited from a respective control pulse while executing the closed loop policy;
wherein the expected range of the value of the characteristic comprises an ECAP high threshold (ETH) and an ECAP low threshold (ETL), and wherein the method further comprises:
responsive to the value of the characteristic of the ECAP signal greater than the ECAP high threshold, incrementally adjusting:
a respective value of the parameter defining the plurality of respective control pulses from a first control pulse value toward a second control pulse value; and
a respective value of the parameter defining the plurality of respective informed pulses from a first informed pulse value toward a second informed pulse value.

5. The method of claim 4, further comprising:
responsive to disabling the closed loop policy, adjusting, by the processing circuitry, informed pulse parameter values back to the first informed pulse value, and
measuring, by the sensing circuitry, the respective ECAP signal after the respective control pulse, wherein the processing circuitry makes no adjustments to informed pulse parameter values nor control pulse parameter values based on the measured respective ECAP signal while the closed loop policy is disabled.

6. The method of claim 5,
wherein the first informed pulse value of the parameter is a control pulse parameter default value,
wherein the second control pulse value is less than or equal to the default value, and
wherein the control pulse parameter is set to the second control pulse value,
the method further comprising, in response to in response to receiving an indication from the sensing circuitry that the value of the characteristic of the measured respective ECAP signal is less than the ECAP low threshold, start a low-noise timer;
responsive to determining that the low-noise timer has expired, adjusting, by the processing circuitry, the control pulse parameter values from the second control pulse value to the default value.

7. The method of claim 6, further comprising:
responsive to setting the control pulse parameter values to the default value, starting, by the processing circuitry, a confirmation timer, and
responsive to determining that the confirmation timer has expired, enabling, by the processing circuitry, the closed-loop policy.

8. The method of claim 6, further comprising:
responsive to sensing, by the sensing circuitry, that the value of the characteristic of the measured respective ECAP signal is greater than the ECAP high threshold, reducing, by the processing circuitry,
the respective value of the parameter for the plurality of respective control pulses; and
the respective value of the parameter for the plurality of respective informed pulses.

9. The method of claim 8, further comprising:
responsive to determining that the low-noise timer has expired, adjusting, by the processing circuitry, control pulse value from the second control value to the default control pulse value,
responsive to setting the control pulse parameter values to the default control pulse value, starting, by the processing circuitry, a confirmation timer, and
responsive to determining that the confirmation timer has expired, enabling, by the processing circuitry, the closed-loop policy.

10. The method of claim 4, further comprising, responsive to sensing, by the sensing circuitry, that the value of the characteristic of the measured respective ECAP signal is less than the ECAP high threshold, starting, by the processing circuitry a low-noise timer.

11. The method of claim 10, further comprising, responsive to determining, by the processing circuitry, that the low-noise timer has expired, enabling, by the processing circuitry, the closed-loop policy.

12. The method of claim 1, further comprising controlling the stimulation generation circuitry to deliver electrical stimulation therapy according to:
the closed loop policy, or
user input.

13. A medical device comprising processing circuitry configured to:
receive information indicative of a sensed evoked compound action potential (ECAP) signal
determine a value of a characteristic of the ECAP signal based on the information, wherein the ECAP signal is elicited by respective stimulation pulses of a plurality of stimulation pulses;
determine whether the value of the characteristic of the ECAP signal is inside or outside of an expected range of the characteristic;
responsive to determining that the value is inside the expected range, execute a closed loop policy wherein the closed loop policy adjusts a parameter value that at least partially defines stimulation therapy, based on the value of the characteristic of the ECAP signal; and
responsive to determining that the value of the characteristic of the ECAP signal is outside of the expected range, disable the closed-loop policy and set the parameter value to a threshold value;
responsive to setting the parameter value to the threshold value, start a noise detection timer;
responsive to determining that the noise detection timer has expired, enable the closed-loop policy.

14. The medical device of claim 13,
wherein
the processing circuitry further configured to:
responsive to determining that the noise detection timer has expired, and that the value of the characteristic of the ECAP signal is still outside of the expected range, disable the closed-loop policy.

15. The medical device of claim 14, wherein the threshold value of the parameter of the respective stimulation pulses comprises a minimum value for the parameter.

16. The medical device of claim 15:
wherein the plurality of stimulation pulses comprises a plurality of control pulses and a plurality of informed pulses,
wherein the respective stimulation pulses comprise respective control pulses of the plurality of control pulses,
wherein receiving information indicative of a ECAP signal comprises sensing a respective ECAP signal after a respective control pulse of the plurality of control pulses,
wherein an informed pulse of the plurality of informed pulses is defined by one or more parameters based on a respective ECAP signal elicited from a respective control pulse,
wherein the expected range of the value of the characteristic comprises an ECAP high threshold (ETH) and an ECAP low threshold (ETL),
the processing circuitry further configured to, responsive to the value of the characteristic of the ECAP signal greater than the ECAP high threshold, incrementally adjusting:
a respective parameter value for the plurality of respective control pulses from a first control pulse value toward a second control pulse value; and
a respective parameter value for the plurality of respective informed pulses from a first informed pulse value toward a second informed pulse value.

17. The medical device of claim 16, wherein the processing circuitry is further configured to:
responsive to disabling the closed loop policy, adjust the informed pulse parameter values back to the first informed pulse values, and
cause the sensing circuitry to measure the respective ECAP signal after the respective control pulse, wherein the processing circuitry makes no adjustments to the informed pulse parameter values nor the control pulse parameter values based on the measured respective ECAP signal while the closed loop policy is disabled.

18. The medical device of claim 17, wherein the processing circuitry further configured to, responsive to receiving an indication from the sensing circuitry that the value of the characteristic of the measured respective ECAP signal is less than the ECAP high threshold, start a low-noise timer.

19. The medical device of claim 18, wherein the processing circuitry is further configured to, responsive to determining that the low-noise timer has expired, enable the closed-loop policy.

20. The medical device of claim 16,
wherein the first informed pulse value of the parameter is a control pulse parameter default value,
wherein the second control pulse value is less than or equal to the default value, and
wherein the control pulse parameter is set to the second control pulse value,
wherein the processing circuitry further configured to:
responsive to receiving an indication from the sensing circuitry that the value of the characteristic of the measured respective ECAP signal is less than the ECAP low threshold, start a low-noise timer; and
responsive to determining that the low-noise timer has expired, adjust the control pulse parameter values from the second control pulse value to the default control pulse value.

21. The medical device of claim 20, wherein the processing circuitry is further configured to,
responsive to setting the control pulse parameter values to the default control pulse value, start a confirmation timer, and
responsive to determining that the confirmation timer has expired, enable the closed-loop policy.

22. The medical device of claim 20, wherein the processing circuitry is further configured to, responsive to receiving an indication from the sensing circuitry, that the value of the characteristic of the measured respective ECAP signal is greater than the ECAP high threshold, reducing the respective parameter value for the plurality of respective control pulses.

23. The medical device of claim 22, wherein the processing circuitry is further configured to,
responsive to determining that the low-noise timer has expired, adjust the control pulse parameter values from the second control pulse value to the default control pulse value,
responsive to setting the control pulse parameter values to the default control pulse value, start a confirmation timer, and
responsive to determining that the confirmation timer has expired, enable the closed-loop policy.

24. The medical device of claim 13, wherein the processing circuitry is further configured to control the stimulation generation circuitry to deliver electrical stimulation therapy according to:
the closed loop policy, or
user input.

25. A non-transitory computer-readable storage medium comprising instructions, that when executed, cause programmable processing circuitry to:
receive information indicative of a sensed evoked compound action potential (ECAP) signal;
determine a value of a characteristic of the ECAP signal based on the information, wherein the ECAP signal is elicited by respective stimulation pulses of a plurality of stimulation pulses;
determine whether the value of the characteristic of the ECAP signal is inside or outside of an expected range of the characteristic;
responsive to determining that the value is inside the expected range, execute a closed loop policy, based on the value of the characteristic of the ECAP signal, wherein the closed loop policy adjusts a parameter value that at least partially defines stimulation therapy;
responsive to determining that the value of the characteristic of the ECAP signal is outside of the expected range, disable the closed-loop policy and set the parameter value to a threshold value;
responsive to setting the parameter value to the threshold value, start a noise detection timer; and
responsive to determining that the noise detection timer has expired, enable the closed-loop policy.

* * * * *